(12) United States Patent
Fensterle et al.

(10) Patent No.: US 8,679,473 B2
(45) Date of Patent: Mar. 25, 2014

(54) NON-PATHOGENIC AND/OR ATTENUATED BACTERIA CAPABLE OF INDUCING APOPTOSIS IN MACROPHAGES, PROCESS OF MANUFACTURING AND USES THEREOF

(75) Inventors: Joachim Fensterle, Hoechberg (DE); Katharina Galmbacher, Munich (DE); Ulf Rapp, Wuerzburg (DE); Werner Goebel, Munich (DE); Christian Hotz, Munich (DE)

(73) Assignee: Aeterna Zentaris GmbH, Frankfurt (DE)

( * ) Notice: Subject to any disclaimer, the term of this patent is extended or adjusted under 35 U.S.C. 154(b) by 0 days.

(21) Appl. No.: 13/364,437

(22) Filed: Feb. 2, 2012

(65) Prior Publication Data

US 2012/0171159 A1 Jul. 5, 2012

Related U.S. Application Data

(62) Division of application No. 12/361,843, filed on Jan. 29, 2009, now abandoned.

(60) Provisional application No. 61/024,225, filed on Jan. 29, 2008.

(30) Foreign Application Priority Data

Jan. 29, 2008 (EP) .................................... 08101045

(51) Int. Cl.
*A01N 63/00* (2006.01)
*A01N 65/00* (2009.01)

(52) U.S. Cl.
USPC .................. 424/93.1; 424/93.2; 424/93.4

(58) Field of Classification Search
None
See application file for complete search history.

(56) References Cited

U.S. PATENT DOCUMENTS

| | | | |
|---|---|---|---|
| 5,589,380 A | 12/1996 | Fasano et al. | |
| 5,972,899 A | 10/1999 | Zychlinsky et al. | |
| 5,976,525 A | 11/1999 | Pace et al. | |
| 6,500,419 B1 * | 12/2002 | Hone et al. | 424/93.2 |
| 2003/0170235 A1 * | 9/2003 | Cohen | 424/143.1 |

OTHER PUBLICATIONS

Xiang et al (Clinical Cancer Research vol. 7, pp. 856s-864s, Mar. 2001).*
Susanna Lewén, et al., "A Legumain-based minigene vaccine targets the tumor stroma and suppresses breast cancer growth and angiogenesis". Cancer Immunology, vol. 57, No. 4, XP009102404, 2008, pp. 507-515.
Arturo Zychlinsky, et al., "IpaB mediates marcophage apoptosis Induced by *Shigella flexneri*", Molecular Microbiology, vol. 11, No. 4, XP009102380, 1994, pp. 619-627.
Lucia Cardenas, et al., "Oral Immunization Using Live Attenuated *Salmonella* spp. as Carriers of Foreign Antigens", Clinical Microbiology Reviews, vol. 5, No. 3, XP000579484, Jul. 1992, pp. 328-342
Beatrice Haimovich, et al., "*Shigella* and *Salmonella*: death as a means of survival", Microbes and Infection, Elsevier. vol. 8, No. 2, XP5294817A, 2006, pp. 568-577.
Li Mei Chen, et al., "*Salmonella* spp. are cytotoxic for cultured macrophages", Molecular Microbiology, vol. 21, No. 5, XP001088211, 1996, pp. 1101-1115.

* cited by examiner

Primary Examiner — Albert Navarro
(74) Attorney, Agent, or Firm — Oblon, Spivak, McClelland, Maier & Neustadt, L.L.P.

(57) ABSTRACT

The invention relates to an non-pathogenic and/or attenuated bacterium which is capable of inducing apoptosis in macrophages.

23 Claims, 28 Drawing Sheets

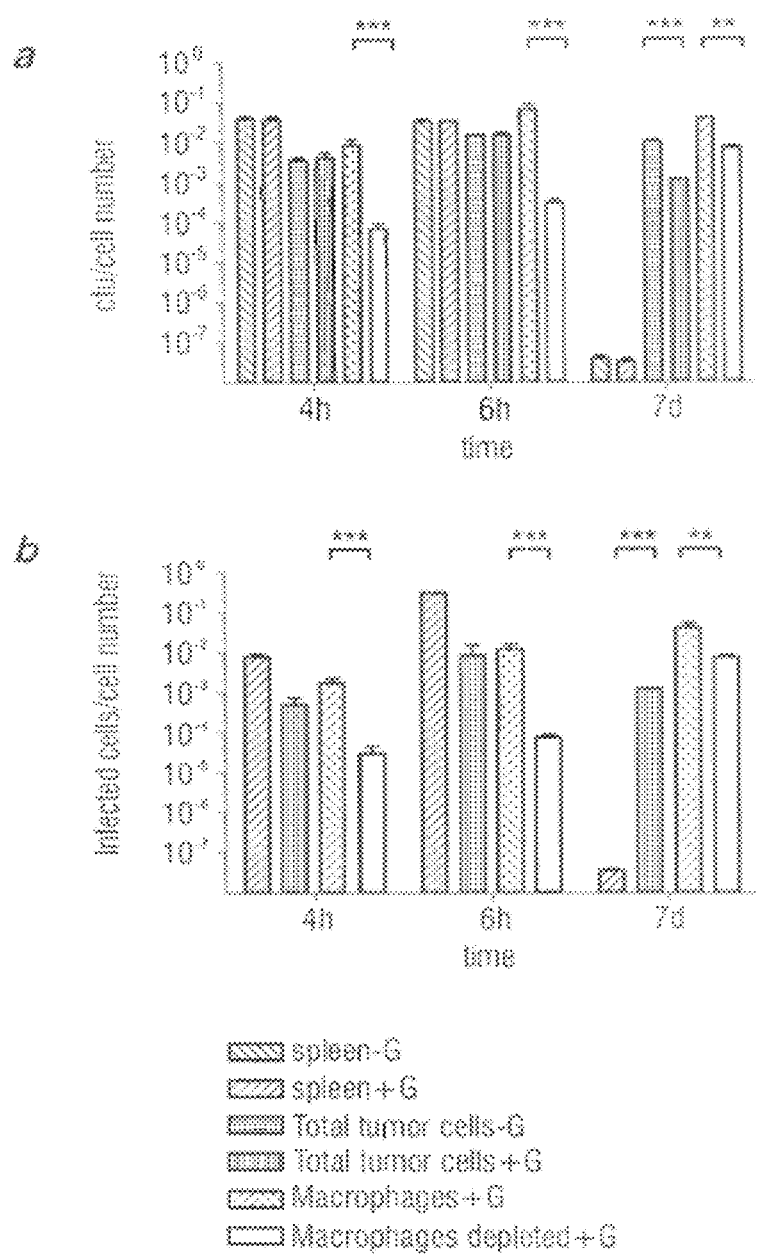

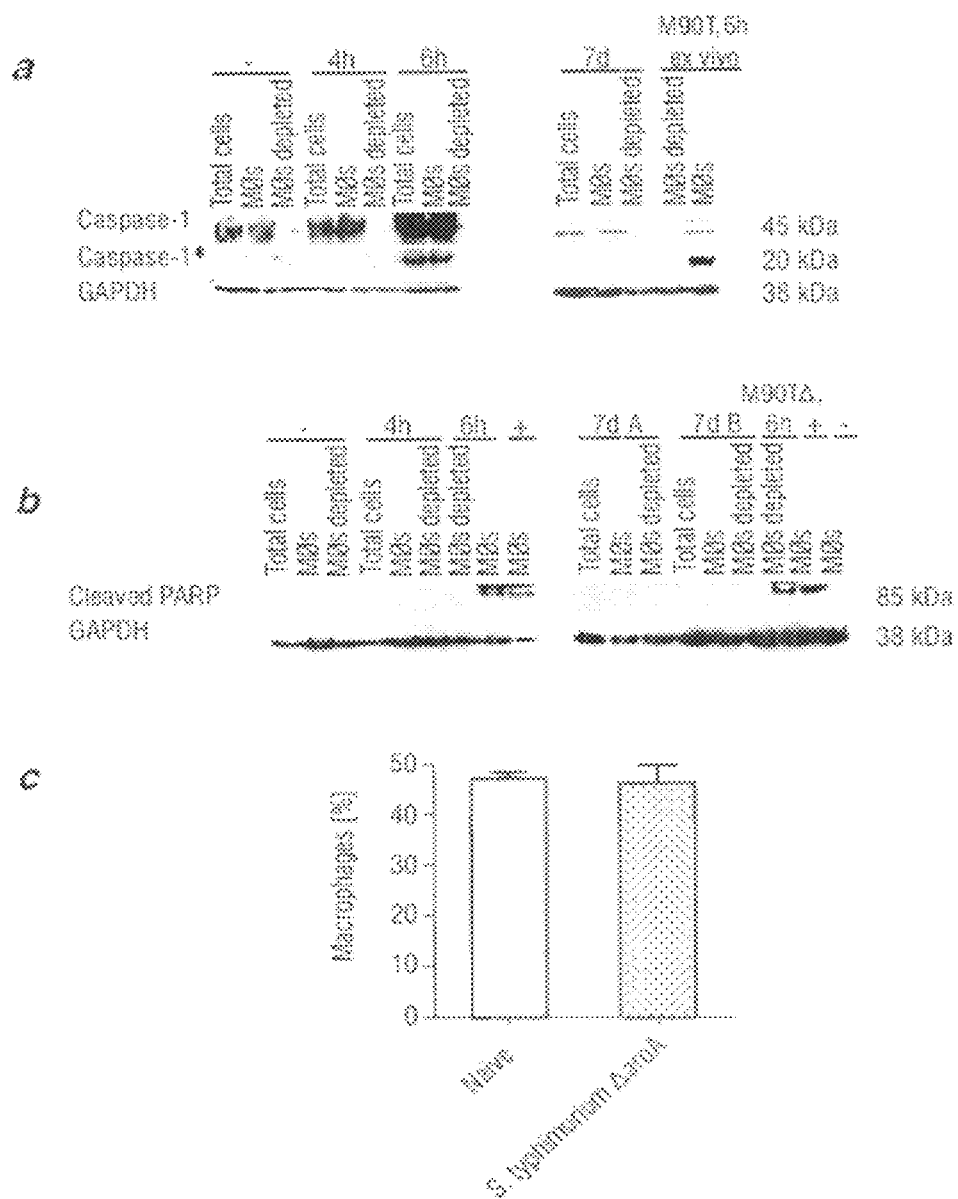

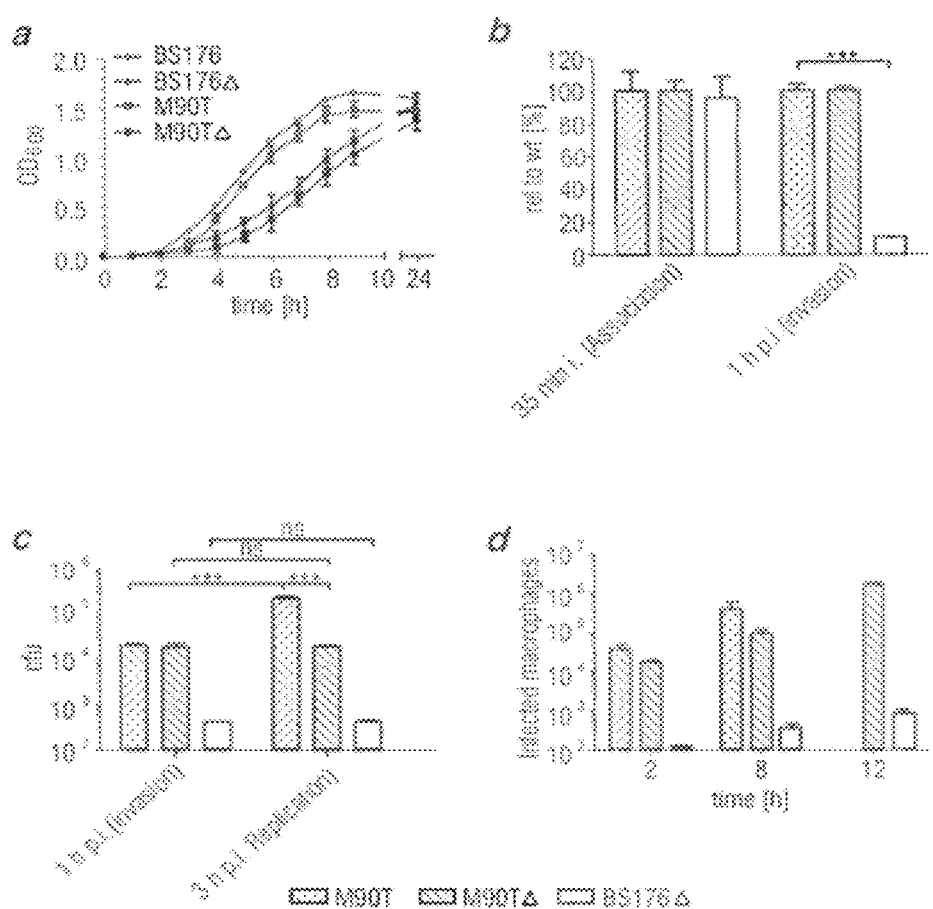
Fig. 4 a-d

Fig. 4 e-g
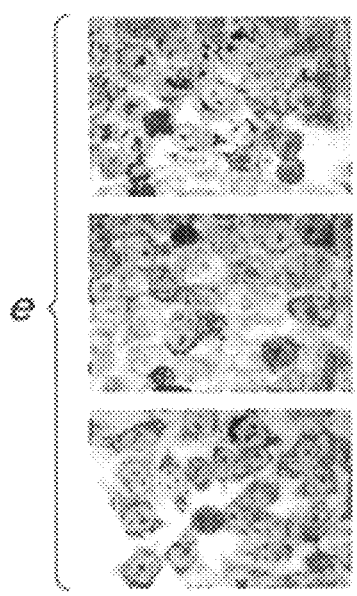
e
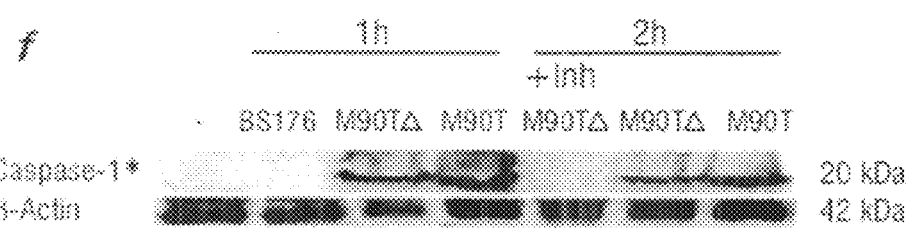
f
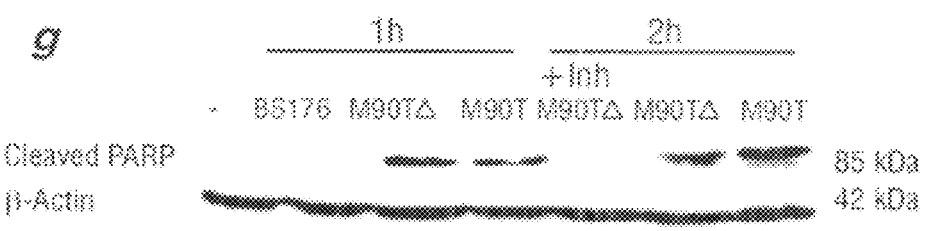
g

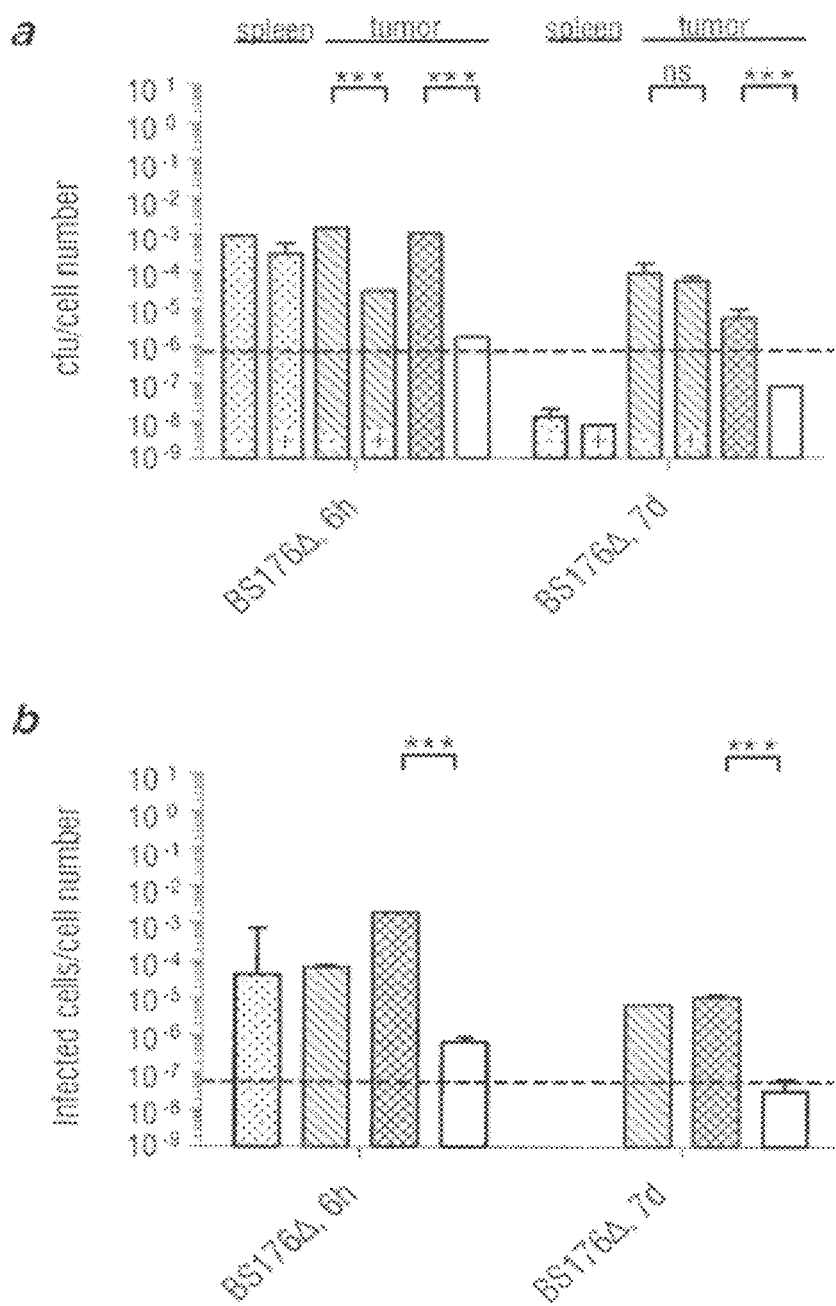

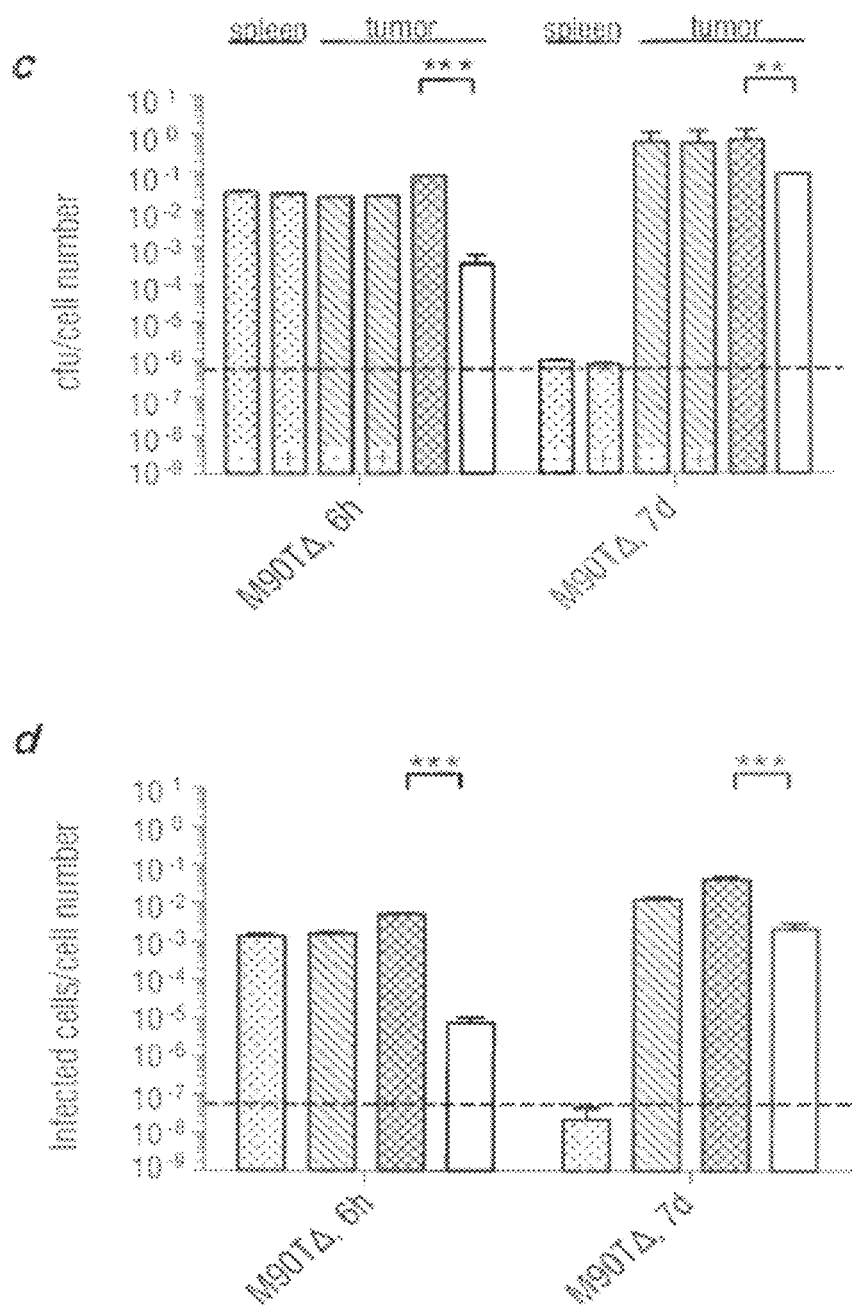

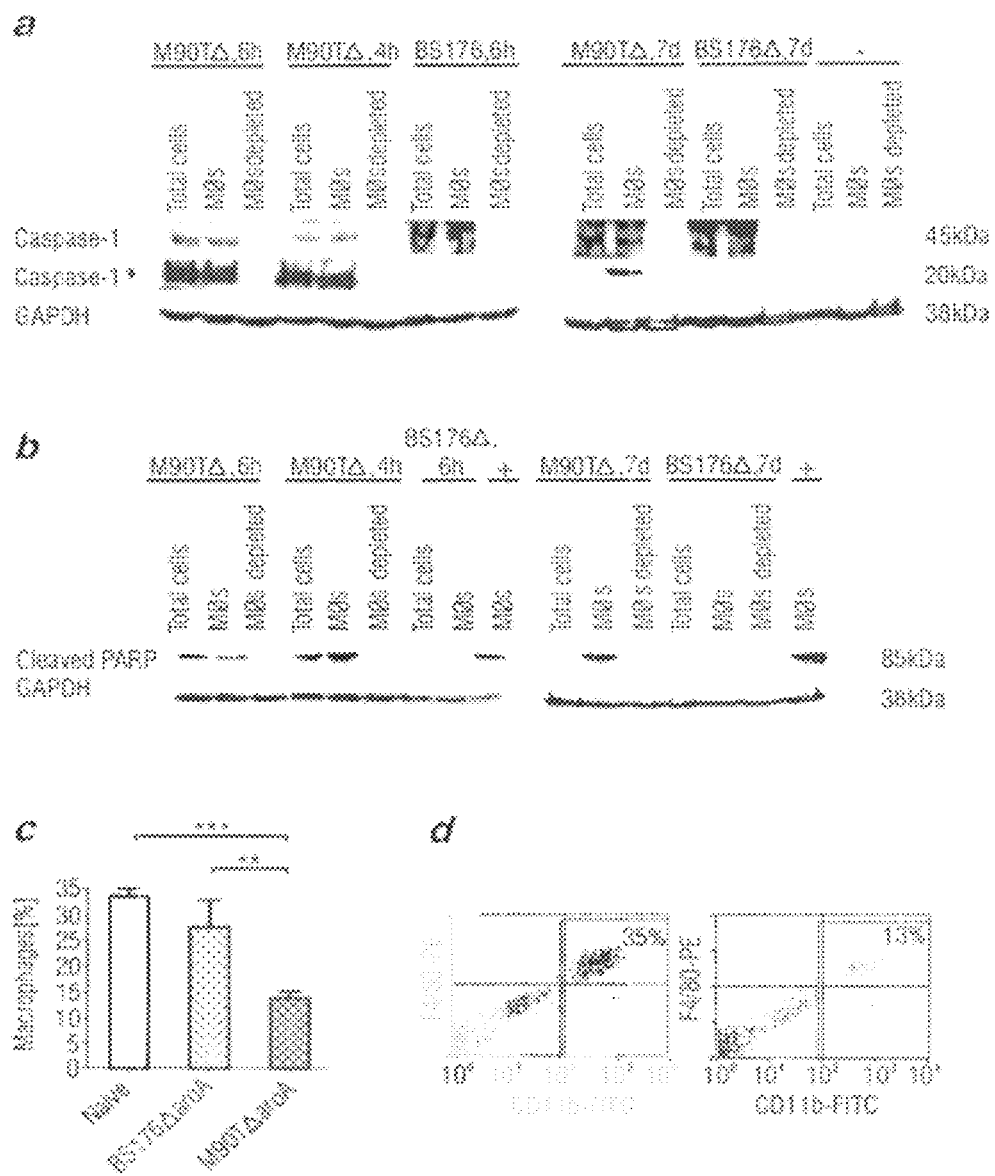
Fig. 6a-d

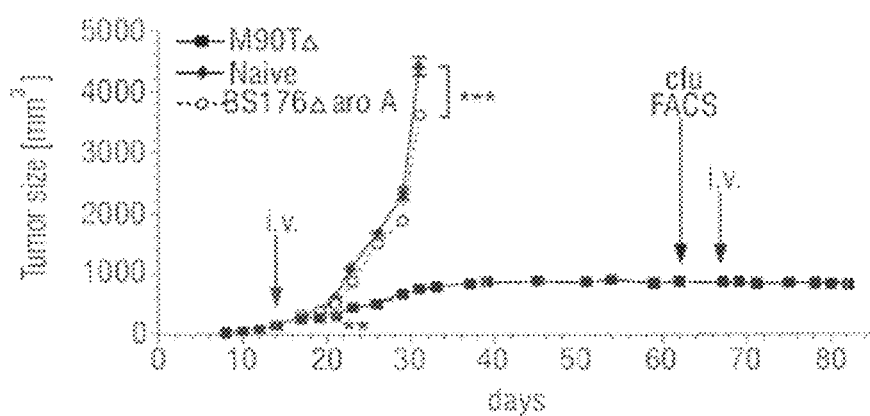
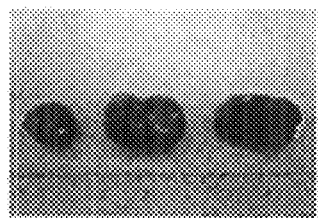
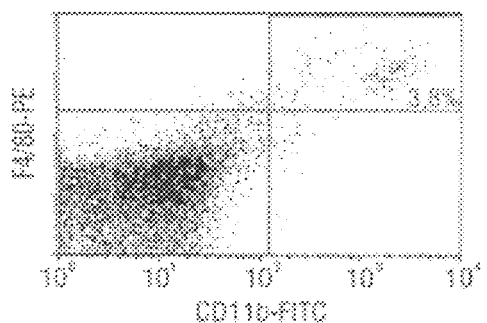
Fig. 2

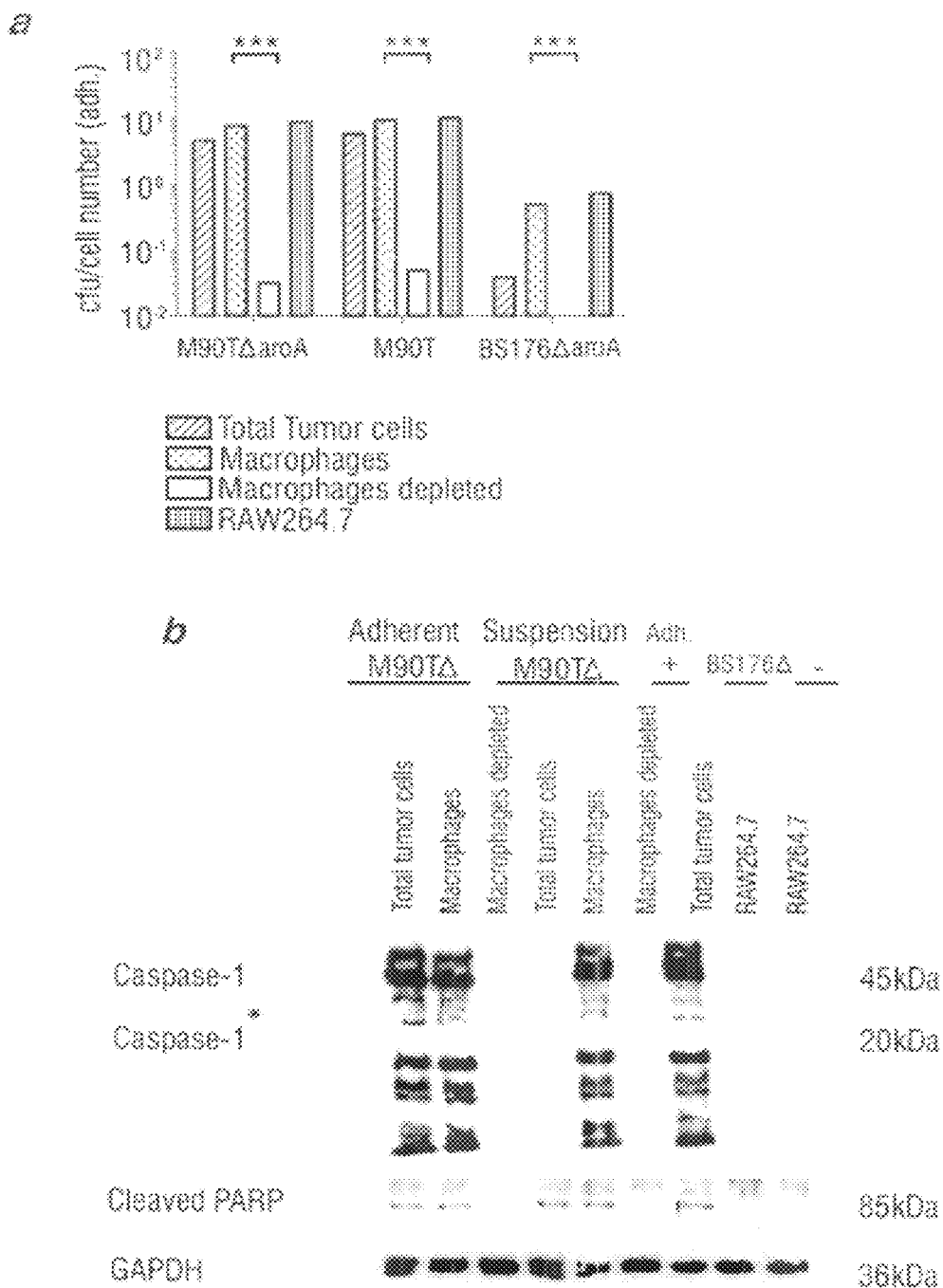

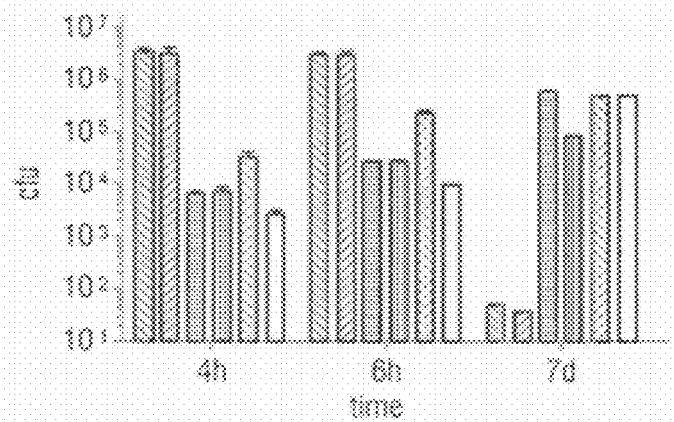
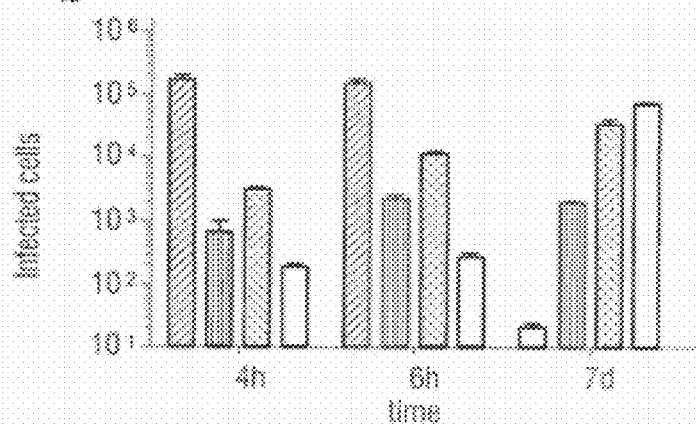
Fig. 15

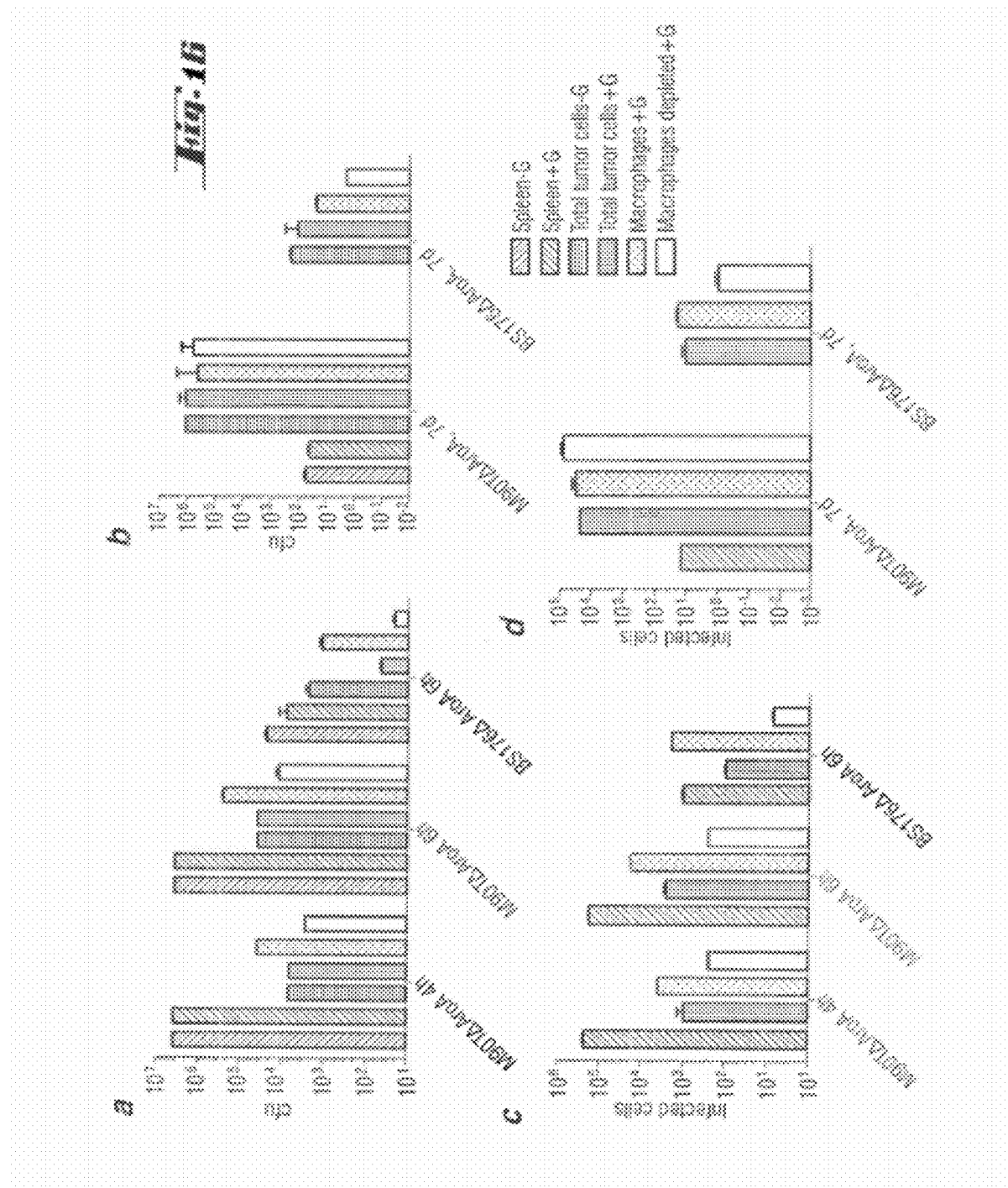

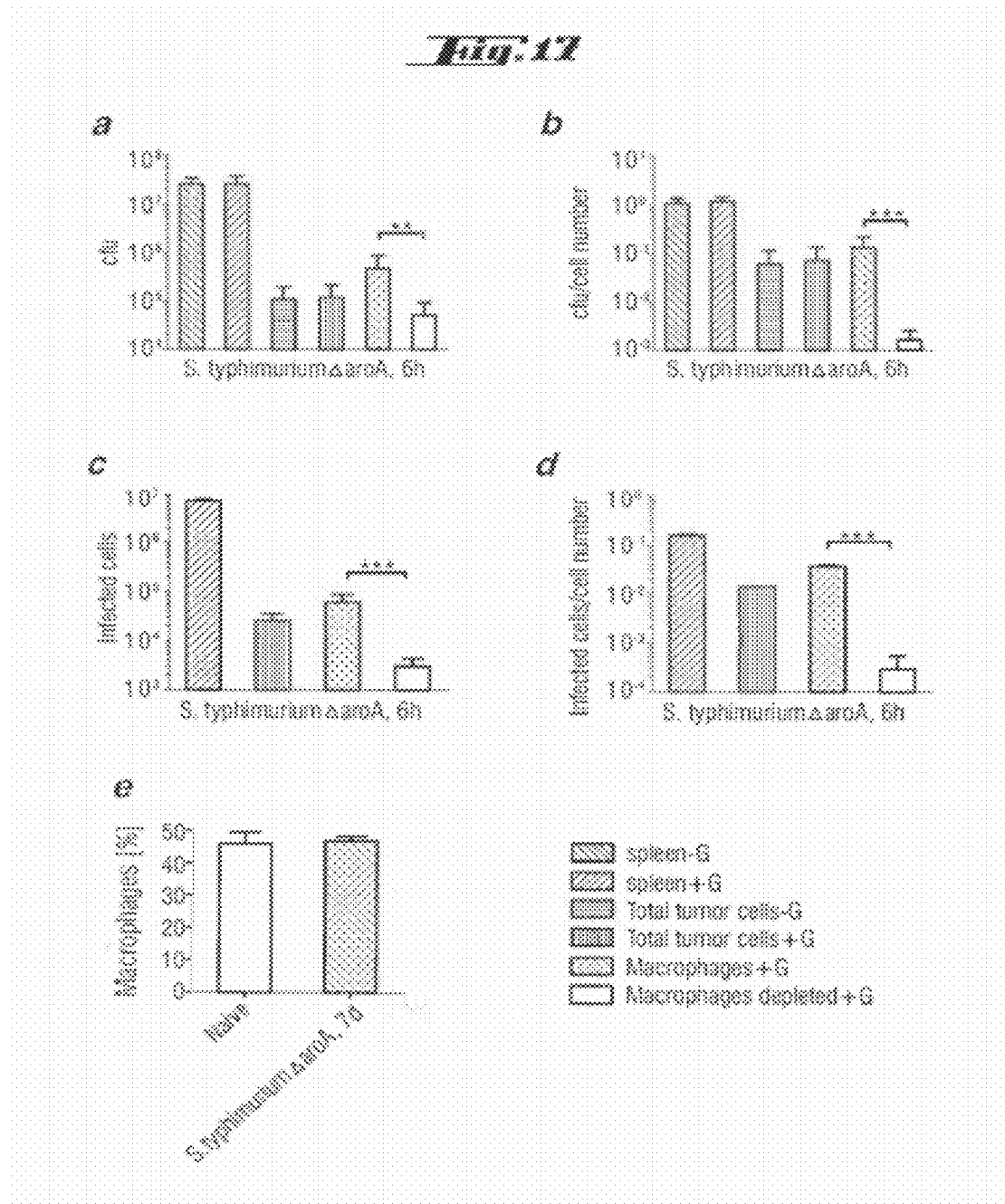

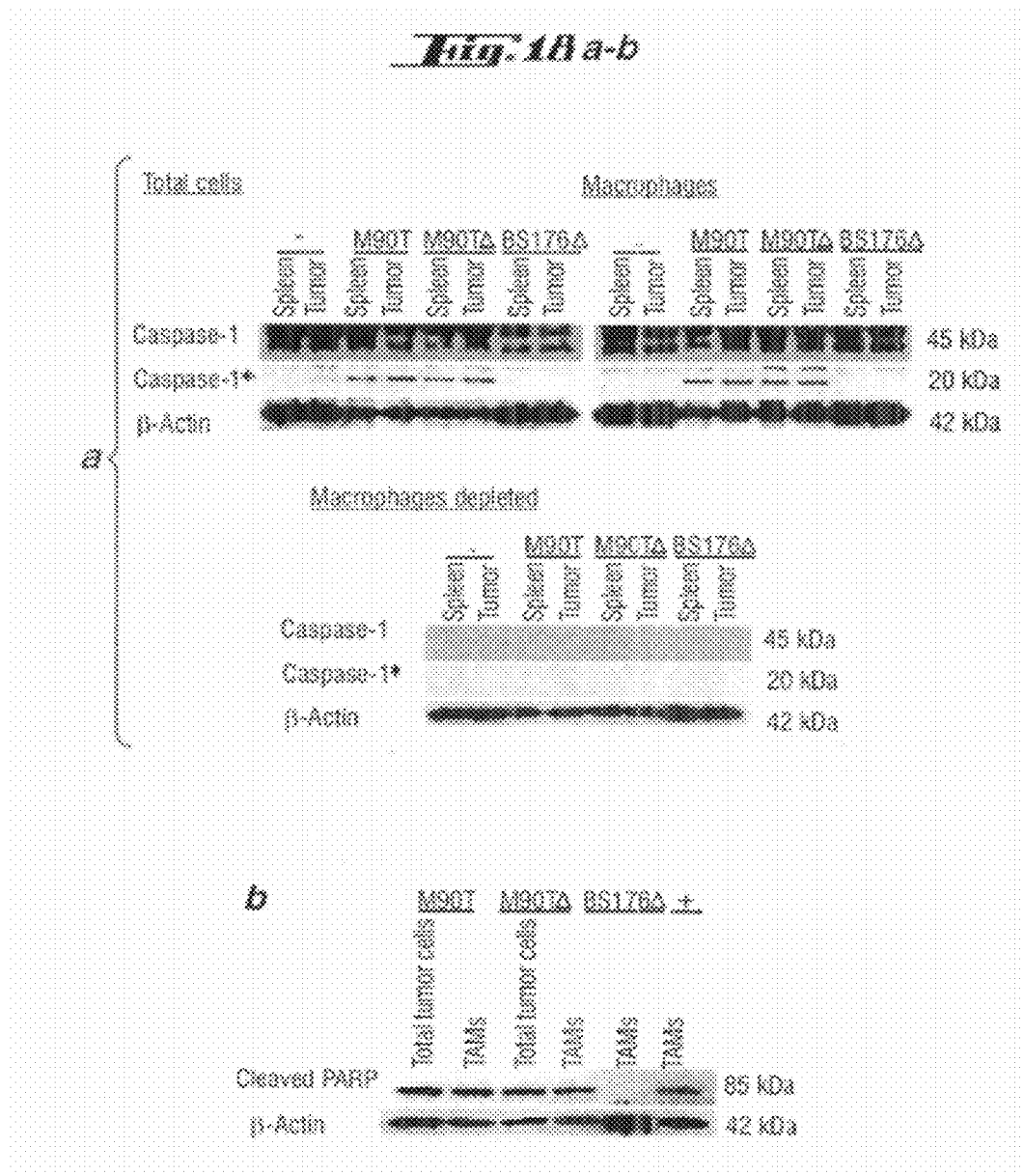

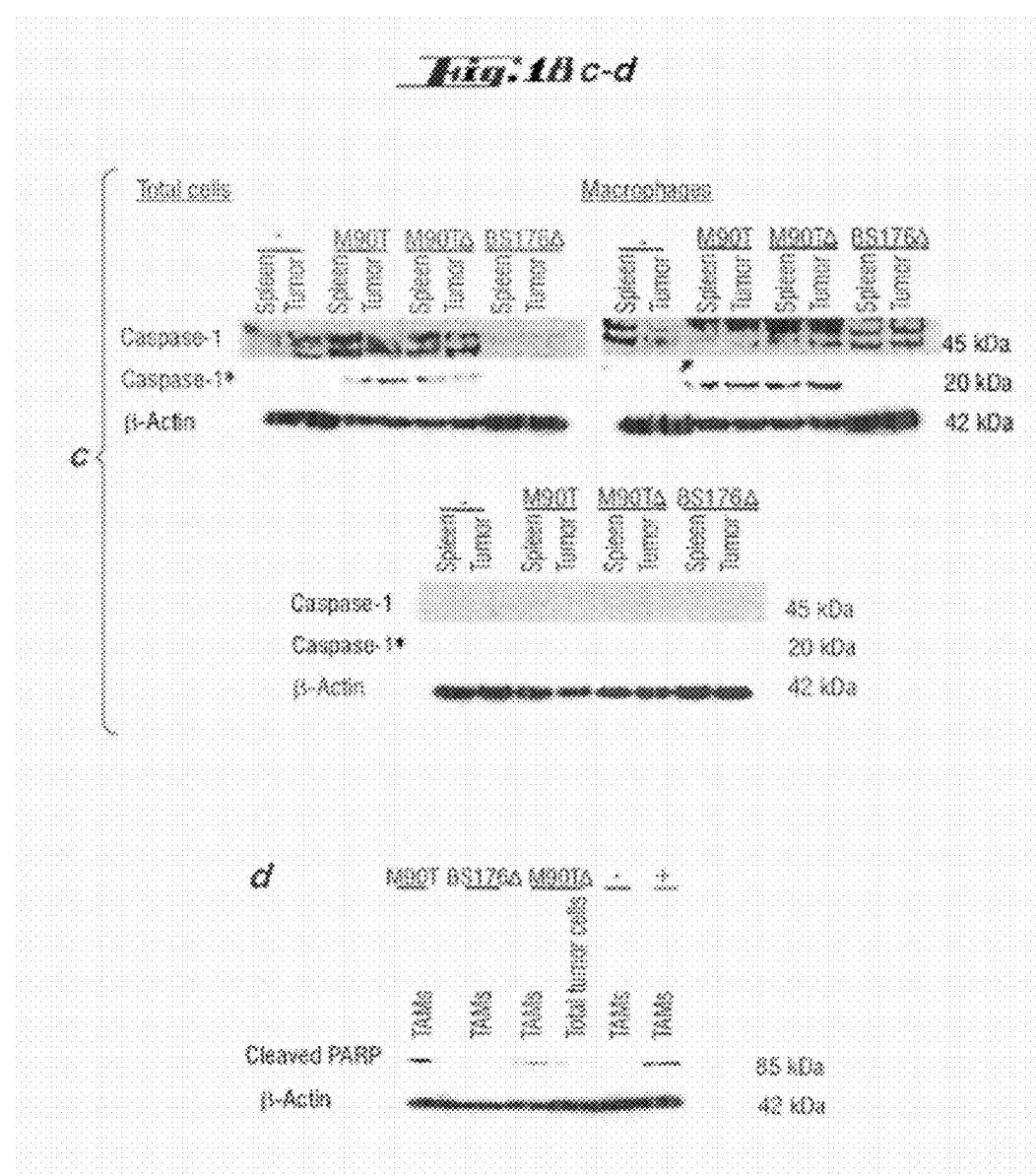

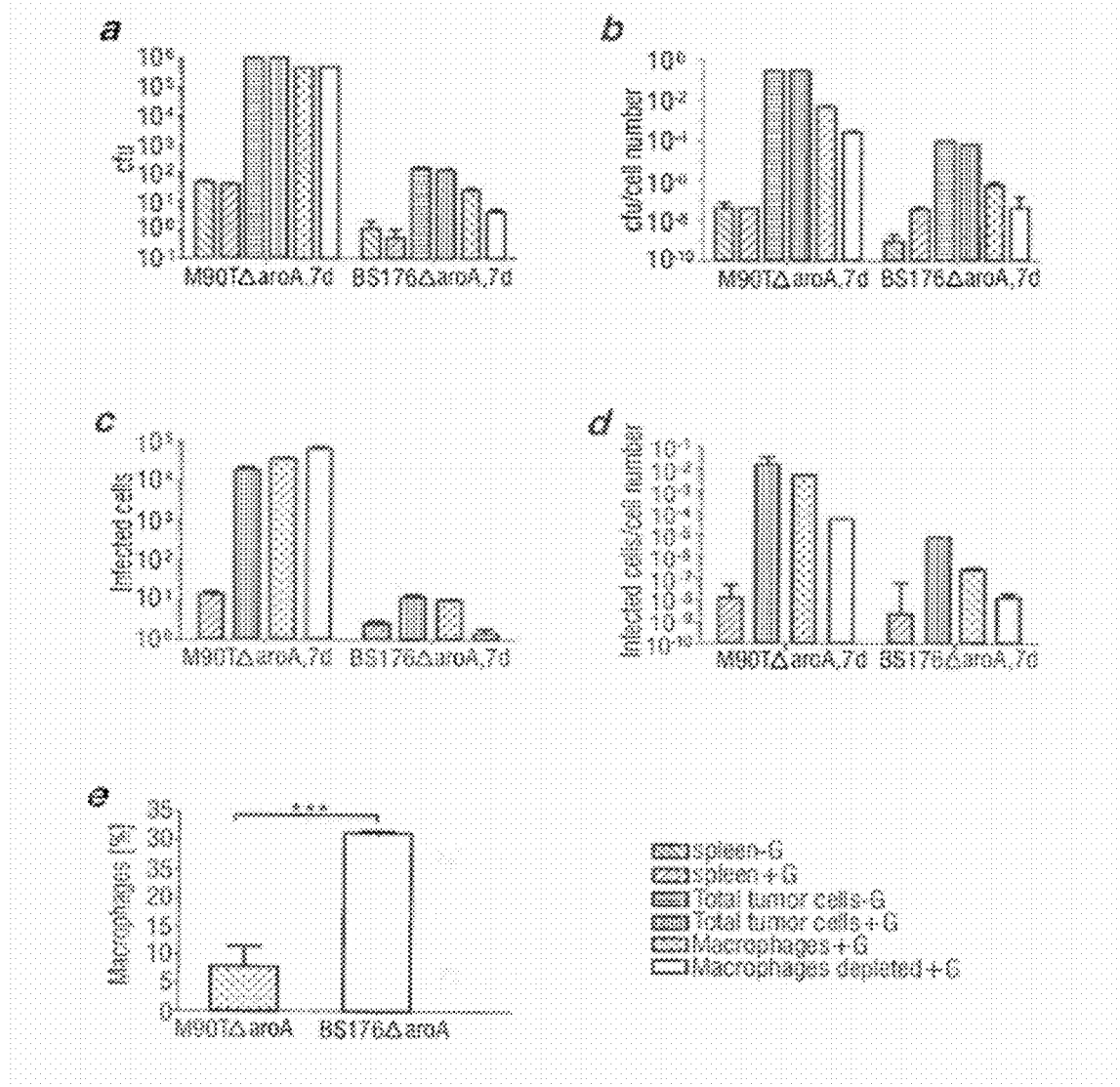

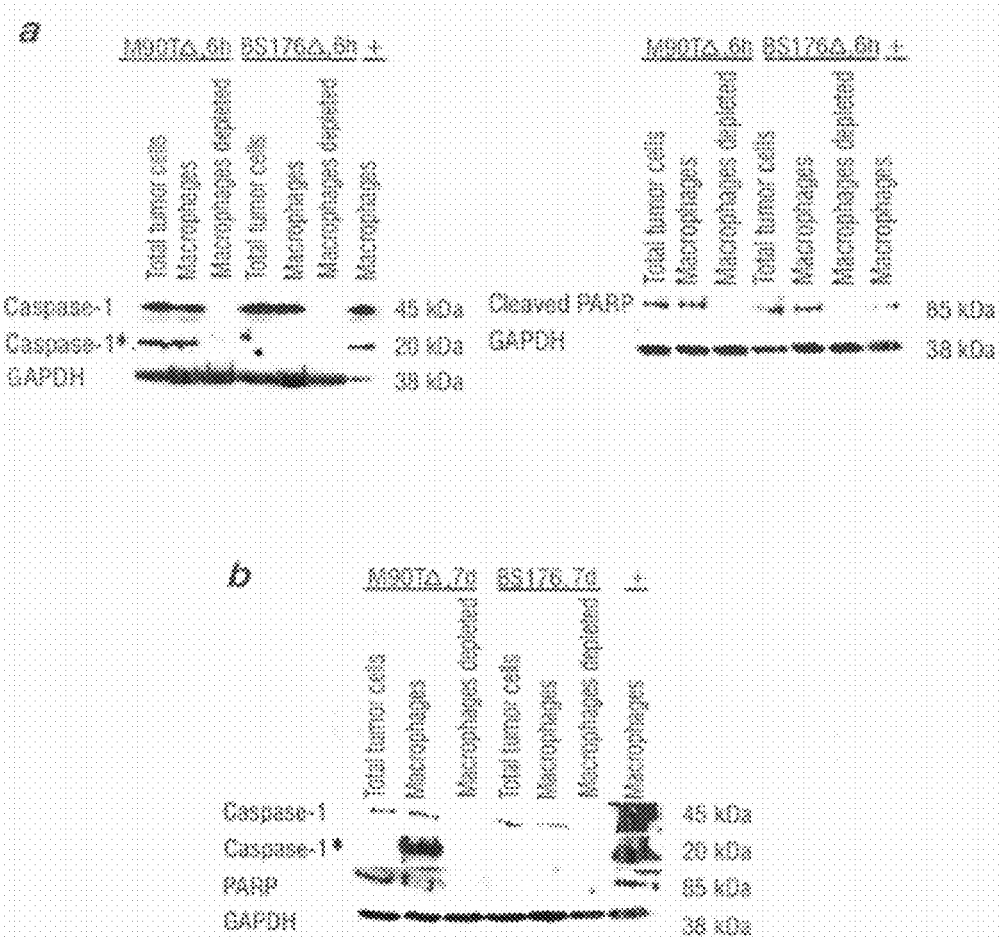

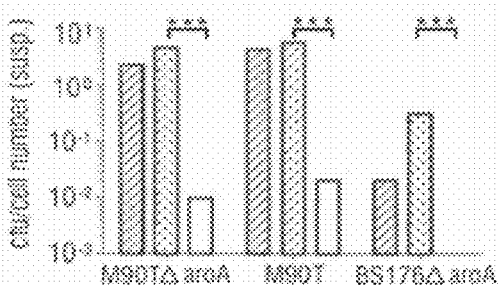
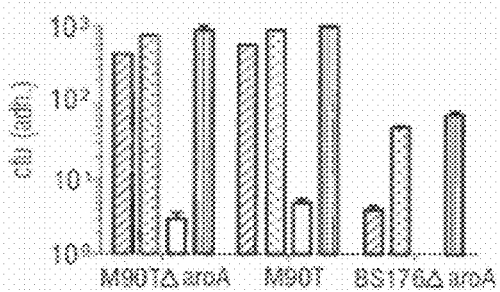
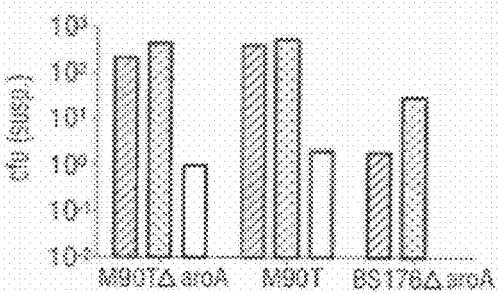
Fig. 21

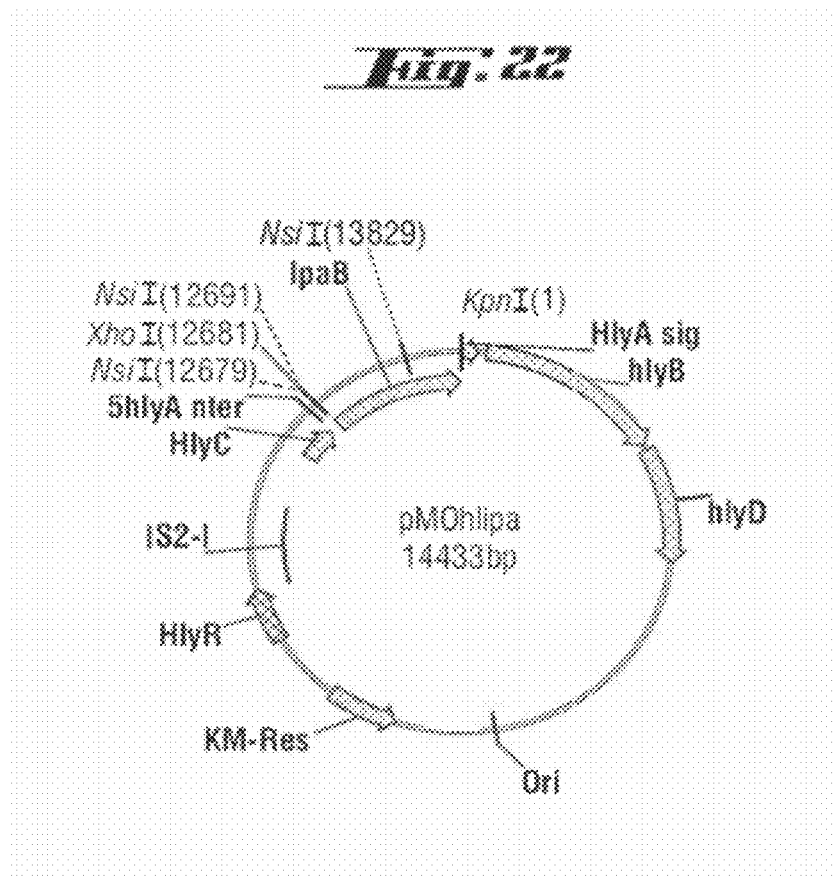

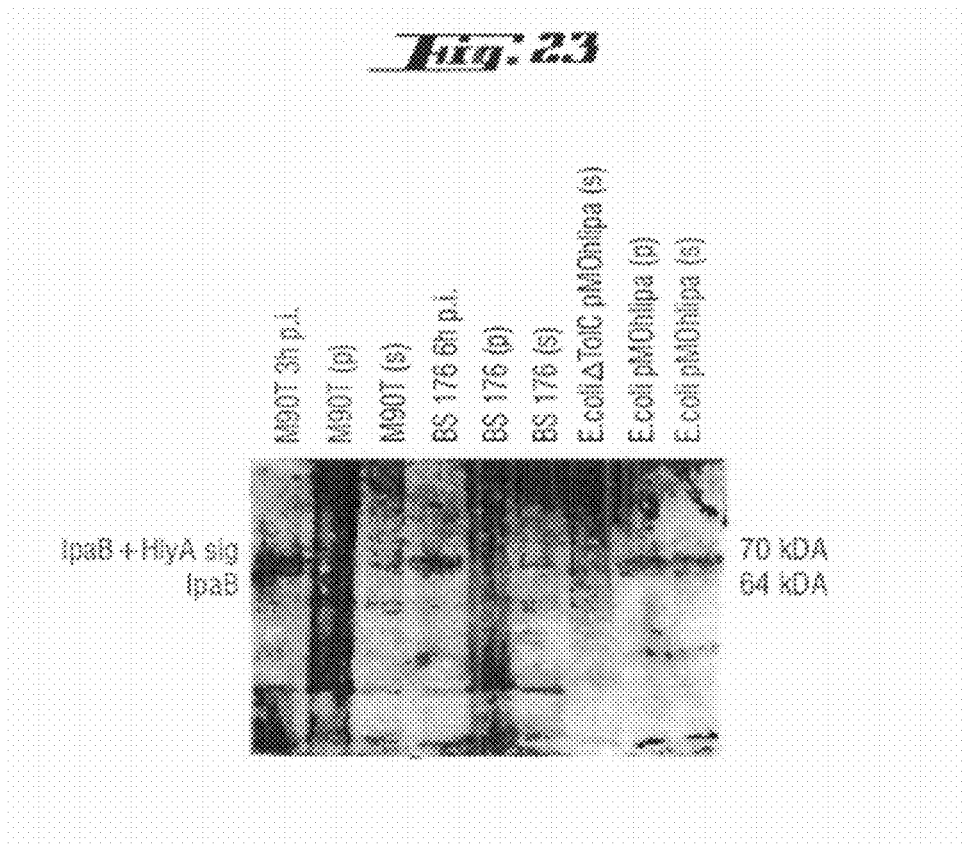

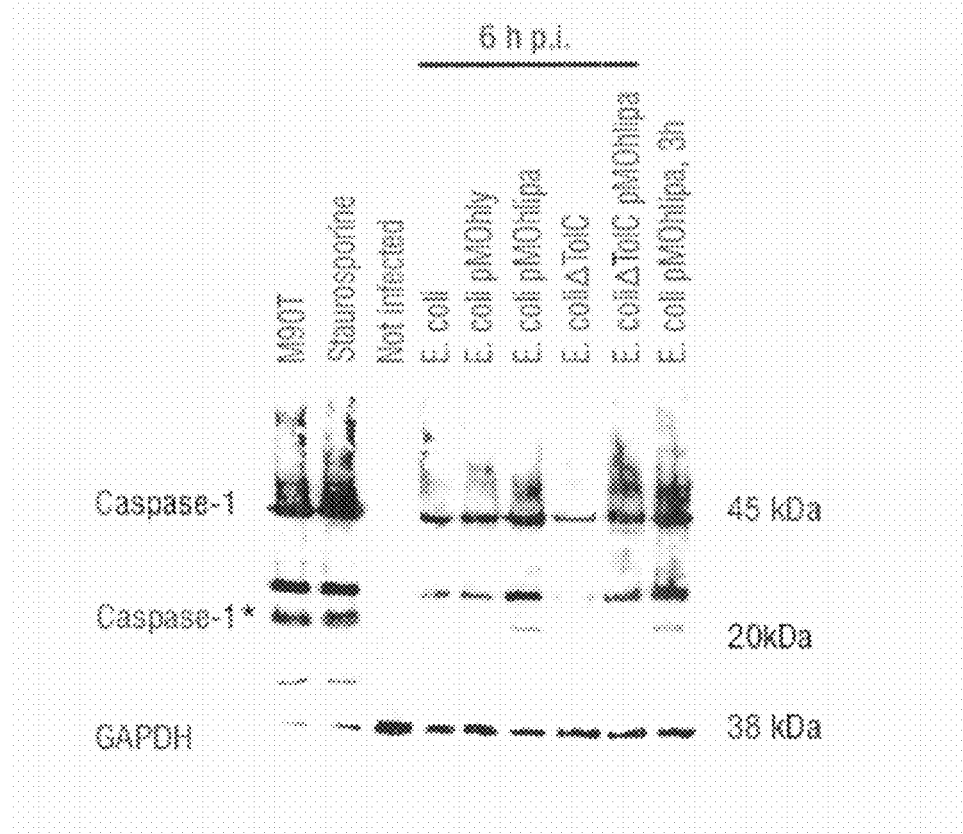

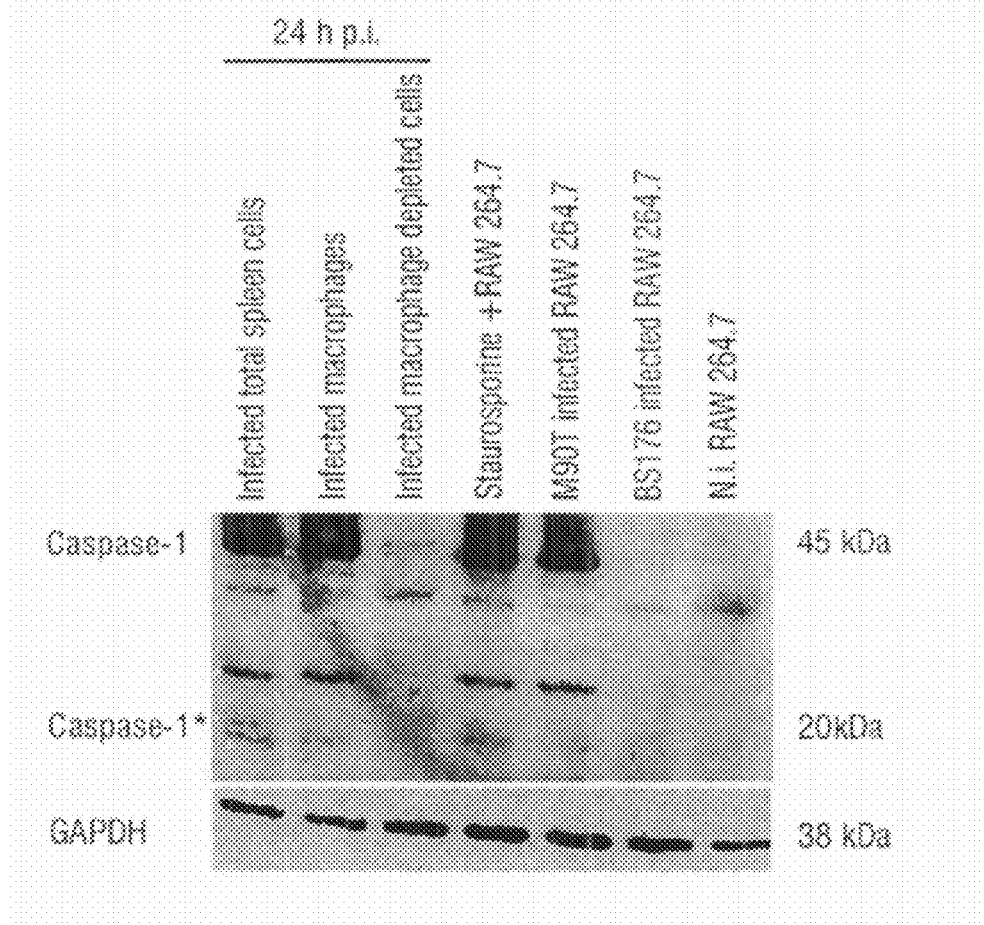

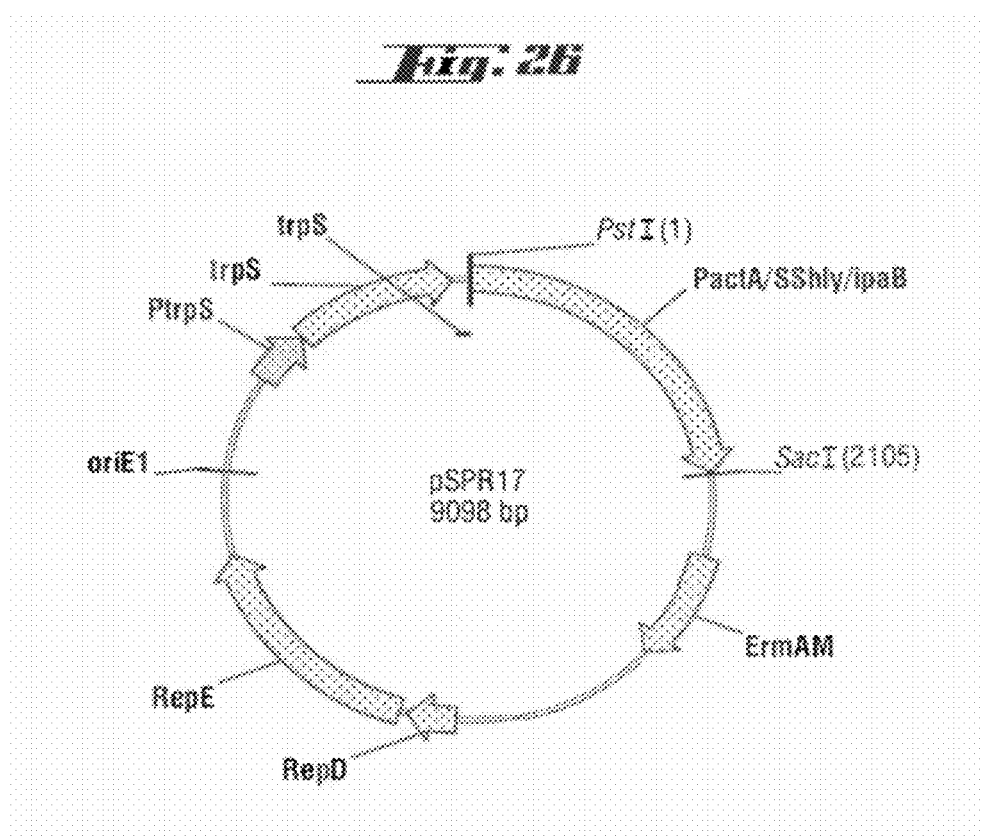

NON-PATHOGENIC AND/OR ATTENUATED BACTERIA CAPABLE OF INDUCING APOPTOSIS IN MACROPHAGES, PROCESS OF MANUFACTURING AND USES THEREOF

CROSS-REFERENCE TO RELATED APPLICATIONS

This application claims the benefit of EP 08101045.6 filed Jan. 29, 2008 and U.S. 61/024,225 filed Jan. 29, 2008, each of which is incorporated herein by reference.

DESCRIPTION OF THE INVENTION

1. Field of the Invention

The invention relates to non-pathogenic and/or attenuated bacteria which are capable of inducing apoptosis in macrophages and a process of manufacturing thereof. These non-pathogenic and/or attenuated bacteria can be used as medicaments, in particular for the treatment of various tumors.

2. Background of the Invention

In 1893, William B. Coley described tumor regression in patients upon acute streptococcal infections (Coley W B, Olin Orthop Relat Res, 1991: 3-11).

Since then, other bacteria have been shown to infiltrate, replicate and then preferentially accumulate in tumors (Yu Y A. et al., Nat Biotechnol 2004, 22: 313-320; Jain R K & Forbes N S, Proceedings of the National Academy of Sciences 2001, 98: 14748-14750; Dang L H et al., Proc Natl Acad Sci USA 2001, 98: 15155-15160; Parker R C et al., Proc Soc Exp Biol Med 1947, 66: 461-467; Malmgren R A & Flanigan C C, Cancer Res 1955, 15: 473-478; Moese J R, Med Klin 1964, 59: 1189-1192; Gericke D et al., Cancer Res 1964, 24: 217-221; Thiele E H et al., Cancer Res 1964, 24: 222-233; Carey R W et al., Eur. J. Cancer 1967, 3: 37-46;; Kohwi Y et al., Gann 1978, 69: 613-618; Brown J M & Giaccia A J, Cancer Res 1998, 58: 1408-1416; Fox M et al., Gene Ther. 1996, 3: 173-178; Lemmon M et al., Gene Ther. 1997, 4: 791-796; Sznol M et al., J Clin Invest 2000, 105: 1027-1030; Low K B et al., Nat Biotechnol 1999, 17: 37-41; Clairmont C et al., J Infect Dis 2000, 181: 1996-2002; Yazawa K et al., Cancer Gene Ther 2000, 7: 269-274; Yazawa K. et al., Breast Cancer Res Treat 2001, 66: 165-170; Kimura N T et al., Cancer Res 1980, 40: 2061-2068).

Several factors have been proposed to be responsible for the bacterial enrichment in tumors. The abnormal vascular supply found in tumors is considered an important factor for bacterial colonisation of the tumor. As tumors or metastases develop, they stimulate angiogenesis to promote the formation of new blood vessels. However, the newly formed vessels are highly disorganised with incomplete endothelial linings and blind ends, resulting in sluggish blood flow and inefficient delivery of nutrients and oxygen to the tumor or metastases. The disorganized and leaky structure of the blood vessels might facilitate entry of bacteria into the tumor tissue and tumor growth with insufficient vascularization leads to multiple regions of hypoxia and anoxia within the tumor (Jain R K & Forbes N S, Proceedings of the National Academy of Sciences 2001, 98: 14748-14750; Dang L H et al., Proc Natl Acad Sci USA 2001, 98: 15155-15160; Brown J M, Cancer Res 1999, 59: 5863-5870; Vaupel P W, Tumour Oxygenation. Gustav Fischer Verlag 1995, 219-232).

The combination of poor nutrient delivery and oxygen starvation results in non-proliferating hypoxic/anoxic cells within tumors and promotes growth of extracellular anaerobic (like Clostridia) and facultative anaerobic bacteria like E. coli (Jain R K & Forbes N S, Proceedings of the National Academy of Sciences 2001, 98: 14748-14750; Dang L H et al., Proc Natl Acad Sci U S A 2001, 98: 15155-15160; Brown J M, Cancer Res 1999, 59: 5863-5870; Vaupel P W, Tumour Oxygenation. Gustav Fischer Verlag 1995, 219-232).

The anti-tumor effect of the extracellular bacteria, like genetically modified obligate anaerob *Clostridia*, was attributed to the local production of factors toxic for tumor cells in hypoxic areas and the induction of inflammation (Agrawal N at al., Proc Natl Acad Sci U S A. 2004, 101(42): 15172-15177).

Also facultative intracellular bacteria like *Salmonella* were used for tumor therapy and were effective in some experimental models (Jain R K & Forbes N S, Proceedings of the National Academy of Sciences 2001, 98: 14748-14750; Low K B et al., Nat Biotechnol 1999, 17: 37-41; Clairmont C et al., J Infect Dis 2000, 181: 1996-2002; Pawelek, J. M., Low, K. B. and Bermudes, D. Cancer Res. 1997, 57: 4537-4544. Again, it was speculated that the induction of an inflammatory response is mediating the anti-tumor effect. However, the efficacy of *Salmonella* as an anti-tumor agent in humans was only modest.

More recently, the use of intracellular bacteria for DNA delivery into eukaryotic cells has been described. Therefore, intracellular bacteria like *Salmonella, Shigella* or *Listeria* could be employed to deliver therapeutic molecules like toxins or pro-drug converting enzymes directly into tumor cells. In contrast to the induction of an inflammatory response or therapeutic approaches with extracellular bacteria, the efficacy of tumor targeting of intracellular bacteria is dictated by the fraction and nature of tumor cells which are infected.

However, at this point no quantitative information is available about the fraction of tumor cells infected by intracellular bacteria and also the nature of the infected cells is not known.

Indeed, tumors are not exclusively composed of malignant cells but rather consist of a complex mixture of transformed cells and tumor stroma. In addition, non-transformed stromal cells frequently display a distinct phenotype compared to equivalent cells in their physiological surrounding. In many tumors, cells belonging to the monocyte-macrophages lineage are a major component of the leucocyte infiltrate of neoplasms. Tumor-associated macrophages (TAMs) originate from circulating blood monocytes. Their recruitment and survival in situ is directed by tumor-derived cytokines and by chemokines (Mantovani A et al., Immunol Today 1992, 13: 265-270). In this context, the term TAM is used describing F4/80$^{30}$ CD11b$^+$macrophages residing in the tumor without implying additional functional characteristics.

Histologically, many macrophages seem to accumulate in or adjacent to poorly vascularized, hypoxic sites, where considerable tissue damage may have occurred. High macrophage numbers have been reported in avascular and necrotic sites in breast, (Leek R D et al., Cancer Res 1996, 56: 4625-4629; Leek R D et al., Br J Cancer 1999, 79: 991-995; Lewis J S at al., J Pathol 2000, 192: 150-158) and ovarian (Negus R P et al., Am J Pathol 1997, 150: 1723-1734) carcinomas and are associated with negative prognosis. The intratumoral milieu, including hypoxia, can induce marked changes in the secretory activity of macrophages eliciting the release of both, pro-angiogenic and inflammatory cytokines by macrophages, which is also evident in the expression of distinct surface markers like CD206 (Cazin M. et al. Eur Respir J 1990, 3: 1015-1022; Yun J K et al. Proc Natl Acad Sci USA 1997, 94: 13903-13908; Tsukamoto Y et al. J Clin Invest 1996, 98: 1930-1941; Rymsa B et al., Res Commun Chem Pathol Pharmacol 1990, 68: 263-266; Rymsa B et al., Am J Physiol 1991, 261: G602-G607; Leeper-Woodford S K &

Mills J W Am J Respir Cell Mol Biol 1992, 6: 326-334; Luo Y et al. J Clin Invest 2006, 116: 2132-2141).

Some authors have characterized TAMs as M2 macrophages expressing several protumoral functions, including promotion of angiogenesis, matrix remodelling and suppression of adaptive immunity (Mantovani A et al., Cancer Metastasis Rev 2006, 25: 315-322; Luo Yet al. J Clin Invest 2006, 116: 2132-2141; Mantovani A et al., European Journal of Cancer 2004, 40: 1660-1667). Furthermore, most TAMs also appear to have defective production of reactive oxygen and nitrogen intermediates when compared with macrophages cultured in vitro (Siegert A et al., Immunology 1999, 98: 551-556; Murdoch C et al., Int J Cancer 2005, 117: 701-708) and are impaired in phagocytosis. These defects might contribute considerably to the prolonged enrichment of bacteria in tumor tissues, including apathogenic bacteria which are readily eliminated by phagocytic cells under normal conditions, despite the presence of large numbers of macrophages.

Recently, Weibel et al. (Weibel et al., Cell Microbiol 2008, Postprint; doi: 10.1111/j.1462-5822.2008.01122.x) have shown that obligate extracellular bacterium *Escherichia coli* K12 localises and replicates within the tumor tissues in regions where also macrophages are located. The authors have shown that the major part of bacteria resides extracellulary and only some bacteria are uptaken by macrophages, which, however, was only demonstrated histologically. Of note, the presence of the bacteria resulted in a, at least partial, reprogramming of the macrophages from a M2 phenotype towards an M1 phenotype. However, the treatment failed to show any therapeutic effect in the 4T1 breast cancer model.

In contrast to extracellular bacteria, pathogenic intracellular bacteria have developed strategies to survive within macrophages. Importantly, phagocytic cells like macrophages or dendritic cells are the primary target of oral intracellular pathogens including *Salmonella, Shigella* and *Listeria*. Under physiological conditions, a systemic application of these bacteria would lead to their elimination from the blood stream by phagocytic cells in spleen, liver or the intestine. Within the macrophage, *Salmonella* and *Shigella* can survive using distinct virulence mechanisms. Of note, both species can induce further inflammation and apoptosis of the infected macrophages through activation of caspase-1 mediated by the IpaB (*Shigella*) and SipB (*Salmonella*) protein which are secreted via type III secretion systems (TTSS) (Suzuki T et al., J Biol Chem 2005, 280: 14042-14050; Zychlinsky A. et al., Mol Microbiol 1994, 11: 619-627; Chen L M et al., Mol Microbiol 1996, 21: 1101-1115; Hilbi H et al., J. Biol. Chem. 1998, 273: 32895-32900). In contrast to the physiological situation, the phagocytic defects of TAMs, which is also evident for extracellular bacteria as demonstrated by Weibel et al. (Weibel et al., Cell Microbiol 2008, Post-print; doi: 10.1111/j.1462-5822.2008.01122.x), might block the uptake of intracellular bacteria and favour the direct infection of tumor cells.

Further relevant prior art documents are: Sica A et al., Eur. J. Cancer 2006, 42: 717-727; Cardenas L. and Clements J D. Clin Microbiol Rev 1992, 5: 328-342; Forbes, N. S., Munn, L. L., Fukumura, D. and Jain, R. K. Cancer Res. 2003, 63: 5188-5193.

BRIEF DESCRIPTION OF THE DRAWINGS

FIG. 2 *Salmonella typhimurium* delta-aroA predominantly targets TAMs in vivo. Determination of cfu/cell number (a) and infected cells/cell number (b) of separated tumor cells and spleen cells as a control 4 h, 6 h and 7 d after i.v. infection of tumor-bearing mice (n=3 mice per group and timepoint) with $1 \times 10^6$ *S. typhimurium* delta-aroA. Cfu was determined by plating serial dilutions of cell lysate. Infected cell number were determined by plating non-lysed, gentamicin treated cells, in L-Top agar. Columns with stripes top down describe total spleen cells treated without gentamicin and column with bottom-up stripes stand for spleen cells with gentamicin treatment. Columns with horizontal stripes describe the total tumor cell fraction treated without gentamicin. Vertical stripes stand for the total tumor cell fraction gentamicin treated. The black columns describe the macrophages fraction and white columns specify the macrophages depleted fraction. At any timepoint, significantly more bacteria were found in the macrophages fractions compared to macrophage depleted tumor cells. 4 and 6 hours after infection, most bacteria were intracellular, whereas 7 days after infection, 10 fold more bacteria were found extracellularly as determined by cfu numbers in gentamicin treated compared to untreated total tumor cells. AU results shown are mean±SD; : $p<0.01$, *: $p<0.001$, students t-test.

FIG. 3 I.v. infection of tumor-bearing mice with *salmonella* induces caspase-1 processing and apoptosis 6 hours, but not 7 days after infection in tumor-associated macrophages. 4 h, 6 h and 7 d after infection of 4T1 tumor-bearing mice with *salmonella*, caspase-1 activation (a) and PARP cleavage (b) of separated and lysed cells was analyzed by Western Blot. The caspase-1 antibody detects the active 20 kDa subunits of caspase-1, the PARP antibody detects the cleaved PARP fragment of 85 kDa. Caspase-1 activation and PARP cleavage was detectable in total cells and macrophages fractions of tumors from mice 6 hours after infection, but not in the macrophages depleted fraction. 7 days after infection, no caspase-1 or apoptosis was detectable in any fraction. GAPDH was used as loading control. 7 days after infection, the relative amount of TAMs was determined by FACS, bars represent means +/− SD of three tumors analyzed by group (c). *Salmonella* did not affect macrophage numbers 7 days after infection.

FIG. 4 Characterization of the aroA-mutant *Shigella flexneri* strains. (a) Determination of the growth rates at 37° C. at 180 rpm in LB-medium. The overnight-culture was diluted 1:20 for the main culture and OD was measured every hour. The plasmidless avirulent strain *Shigella flexneri* BS176 was characterized by a maximal growth rate of 0.3 OD/h in LB-medium, whereas the virulent strain *Shigella flexneri* M90T had a slightly reduced maximal growth rate of 0.2 OD/h (a). Strains carrying aroA mutations had substantially reduced maximal growth rates. M90Tdelta-aroA had a 2.5 fold slower maximal growth rate than wt *Shigella flexneri* M90T. Again, BS176delta-aroA had a slightly higher maximal growth rate compared to M90Tdelta-aroA. (b) Invasion assay with HeLa-cells. Cells were infected with a MOI of 100:1. 35 min i.(association) and 1 h p.i. (invasion), subsequently the cfus were determined relative to the wt strain M90T. The *S. flexneri* M90Tdelta-aroA strain (M90Tdelta) showed no difference in its adhesion or invasion behaviour compared to the wild type strain, whereas the avirulent strain *S. flexneri* BS176delta-aroA (BS176delta) strain, showed an impaired invasion. (c)

Figure 1:
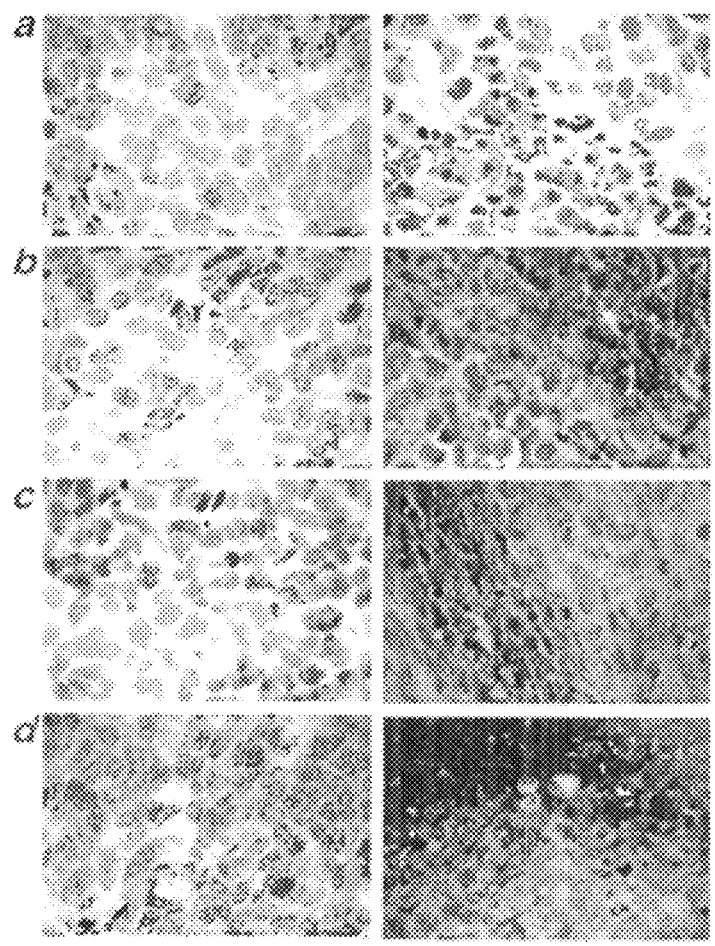
FIG. 1 Substantial amounts of TAMs are detectable in different mouse tumor models. Tumors with diameters of 1-1.5 cm were isolated from mice injected s.c. with $1 \times 10^6$ B78-D14 cells (a), $1 \times 10^4$ 4T1 cells (b) and $1 \times 10^6$ P815-PSA cells (c). In addition, spontaneous breast tumors from transgenic MMTV-Her2/new FVB were isolated (d). Tumor tissue was fixed and embedded in paraffin. Tumor sections were immunostained with a biotinylated anti-F4/80 monoclonal antibody and subsequently counter-stained with Haematoxylin (right). Staining with avidin-horseradish peroxidase without F4/80 antibody was performed as a control (left).

To determine the intracellular replicatory potential, cells were infected with an MOI of 100:1 for 1 hour. Subsequently, cells were incubated for additional 2 hours in the presence of genatamicin and the cfu of lysed cells was determined. The wt strain, but neither M90Tdelta or BS176delta was capable of intracellular replication (d) To determine the ability intercellular spreading, HeLa-cells were infected for 1 h at a MOI of 500:1. After that the infected cells were irradiated for 20 min at 20 Gray to block the replication of the HeLa-cells. The infected, irradiated HeLa-cells were co-incubated with non-infected HeLa-cells in a ratio of 70:1 for 2 h, 8 h and 12 h in the presence of gentamicin. Subsequently, serial dilutions of non-lysed cells in SeaPlaque agarose, were plated out on BHI-agar plates. Cfus of M90Tdelta increased 17 fold 12 h after co-infection, whereas cfus of the avirulent strain BS176delta increased by only 3 fold suggesting a non-impaired potential of M90Tdelta for cell-to-cell spread (e) The cell-to-cell spread capability of M90Tdelta was confirmed by Giemsa staining of HeLa-cells 1 h (supplemental data) and 4 hours after infection. To determine the capacity of the aroA mutants to induce caspase-1 activation and apoptosis induction, J774A.1 mouse macrophages were infected and cellular lysates were analyzed by Western Blotting at different timepoints using a caspase-1 antibody recognizing the active 20 kDa fragment of caspase-1 (f) and a PARP antibody recognizing the cleaved 85 kDa fragment (g). M90Tdelta, but not BS176delta, could induce both caspase-1 induction and apoptosis. Apoptosis induction and caspase-1 processing by M90Tdelta was completely blocked by the caspase-1 specific inhibitor YVAD-CHO (2.5 mM). β-Actin was used as loading control. Bars represent means +/− SD of three different experiments, ***: $p<0.0001$, students t-test.

FIG. 5 *Shigella flexneri* M90Tdelta-aroA predominantly targets TAMs in viva Determination of cfu/cell number (a, c) and infected cells/cell number (b, d) of separated tumor cells and spleen cells as a control 6 h and 7 d after i.v. infection of tumor-bearing mice (n=3 mice per group and timepoint) with *S. flexneri* M90Tdelta-aroA (c, d) and BS176delta-aroA (a, b). Cfu was determined by plating serial dilutions of cell lysate and infected cell number was determined by plating non-lysed, gentamicin treated cells, in L-Top agar. Columns with stripes top down describe total spleen cells treated without gentamicin and column with bottom-up stripes stand for spleen cells with gentamicin treatment. Columns with horizontal stripes describe the total tumor cell fraction treated without gentamicin. Vertical stripes stand for the total tumor cell fraction gentamicin treated. The black columns describe the macrophages fraction and white columns specify the macrophages depleted fraction. At any timepoint, significantly more bacteria are found in the macrophages fraction compared to macrophages depleted tumor cells. At any timepoint, the major part of M90Tdelta-aroA is found intracellularly, whereas 50 fold more bacteria are found extracellularly 6 hours after infection with the avirulent strain BS176delta-aroA (a, b). All results shown are mean±SD; : $p<0.01$, *: $p<0.001$, students t-test.

Figure 6E:
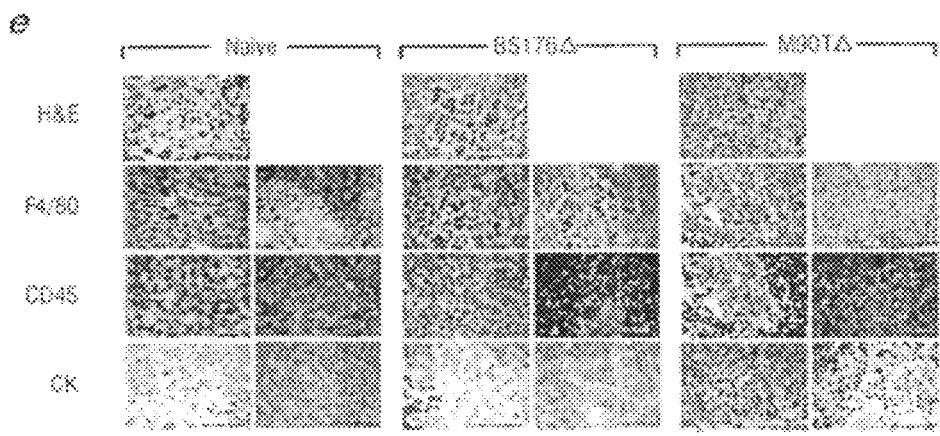

FIG. 6 I.v. infection of tumor-bearing mice with *S. flexneri* M90Tdelta-aroA, but not BS176delta-aroA induces caspase-1 processing and apoptosis 4, 6 hours and 7 days after infection in TAMs and substantially reduces macrophage numbers 7 days after infection. 4 h, 6 h and 7 d after infection of 4T1 tumor-bearing mice with *shigella*, caspase-1 activation (a) and PARP cleavage (b) of separated and lysed cells was analyzed by Western Blot. The caspase-1 antibody detects the active 20 kDa subunits of caspase-1, the PARP antibody detects the cleaved PARP fragment of 85 kDa. Caspase-1 activation and PARP cleavage was detectable in total cells and macrophages fractions of tumors from mice 4 and 6 hours after infection, and in the macrophages fraction 7 days after infection for M90Tdelta, but not BS176delta. GAPDH was used as loading control. 7 days after infection, the relative amount of TAMs was determined by FACS (c), (d); M90Tdelta, but not BS176delta infection resulted in a substantial reduction in macrophage numbers 7 days after infection. Histological examination of naïve, BS176delta and M90Tdelta infected mice (e) revealed a substantial reduction of macrophages (anti-F480 staining,) and intense inflammation (anti-CD45 staining) as well as a almost complete reduction of cytokeratin positive 4T1 tumor cells (anit-CK staining) in tumors derived from M90Tdelta, but not naïve or BS176delta infected mice 7 days after infection. Bars represent means +/− SD of four tumors analyzed by group, : $p<0.01$, : $p<0.001$, Students t-test;

FIG. 7 I.v infection of 4T1 tumor-bearing mice with M90Tdelta, but not BS176delta, blocks tumor growth. (a) 14 days after tumor transplantation, $1\times10^6$ bacteria were applied i.v. to n=8 mice per group. The control group was treated with 1× PBS i.v. There is a substantial reduction in tumor growth and subsequent block of tumor growth after infection with M90Tdelta. Infection with BS176delta results in a small, albeit significant reduction of tumor growth. Naïve and BS176delta infected mice were sacrificed 31 days after tumor inoculation due to animal welfare reasons, n=8 for all groups, n=6 (2 mice were sacrificed to compare tumor growth) and n=3 (3 mice were sacrificed to determine cfu and for FACS analysis) for M90Tdelta infected animals days 1-18, 18-48, 48-68 after the first infection, respectively. : $p<0.01$, *: $p<0.001$. (b) 48 days after infection, macrophage numbers and cfu were determined by FACS and serial dilution respectively. The non-growing tumors exhibited very low macrophage numbers and bacteria were not detectable. At day 49 $1\times10^6$ bacteria were applied i.v. to the remaining 3 mice. No reduction of tumor size was detectable. On day 68 cfu was determined and histological examinations followed. Bacteria were not detectable in tumor, liver and spleen.

FIG. 8 M90Tdelta-aroA predominantly targets TAMs and induces caspase-1 processing and apoptosis in macrophages isolated from human ascites cells ex vivo. (a). Ex vivo infection of the three different cell fraction after cell isolation from a patient with wt *S. flexneri* M90T, *S. flexneri* M90Tdelta-aroA and *S. flexneri* BS176delta-aroA at a MOI of 100:1 for 1 h. After an incubation of 1 h with 300 µ/ml gentamicin serial dilutions were plated on BHI-agar. Next day cfu was determined. Caspase-1 activation and PARP processing in infected cells was analysed by Western Blot (b). The antibody detects the procaspase-1 (45 kDa) and the activated 20 kDa subunit. Note that the macrophage depleted fraction does not contain procaspase-1 in detectable levels. The PARP antibody detects the cleaved PARP fragment of 85 kDa. GAPDH was used as loading control. All results shown are mean±SD; ***: $p<0.001$, students t-test.

Figure 9:
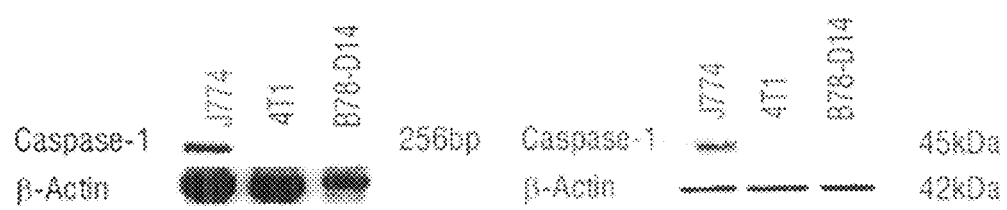

FIG. 9: Caspase-1 is exclusively expressed by macrophages. Analysis of caspase-1 expression by RT-PCR (left) and Western Blot (right). Following primers were used: actin s1 5'-GTCGTACCACAGGCATTGTGATGG-3', actin as 5'-GCAATGCCTGGGTACATGGTGG-3'; Casp1RT_left 5'-TGCCCTCATTATCTGCAACA-3', Casp1RT_right 5'-GGTCCCACATATTCCCTCCT-3

Figure 10:
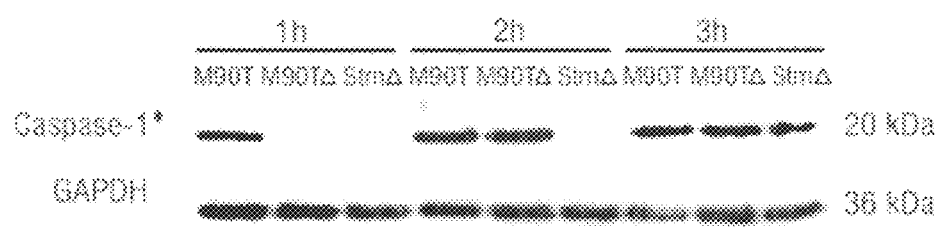
Figure 11:
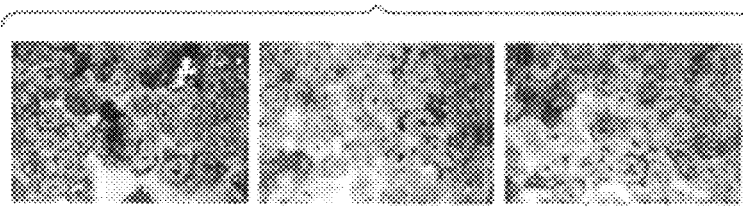

FIG. 10: In vitro activation of Caspase-1 *Salmonella* and *Shigella* in RAW macrophages. RAW 264.7 macrophages were infected at an MOI of 10:1 with *S. flexneri* M90T, *S. flexneri* M90Tdelta-aroA (mid-logarithmic growth phase) and *S. typhimurium* delta-aroA (stationary growth phase) at different time points. Subsequently, a Western Blot for caspase-1 activation of the cell lysate was performed. The *shigella* strain encompassing the aroA deletion showed a slight delay in caspase-1 activation but reached the same activity after two hours as compared to the wild type *shigella* strain. The *salmonella* strain induces caspase-1 processing 3 hours after incubation. *Salmonella* strains harvested in logarithmic phase do not induce caspase-1 processing in this assay (data not shown). For all subsequent infection experiments, strains harvested in stationary phase were used FIG. 11: Giemsa staining of J774A.1 macrophages after 1 h infected with M90T (left), M90Tdelta-aroA (middle) and BS176delta-aroA (right)

Figure 12:
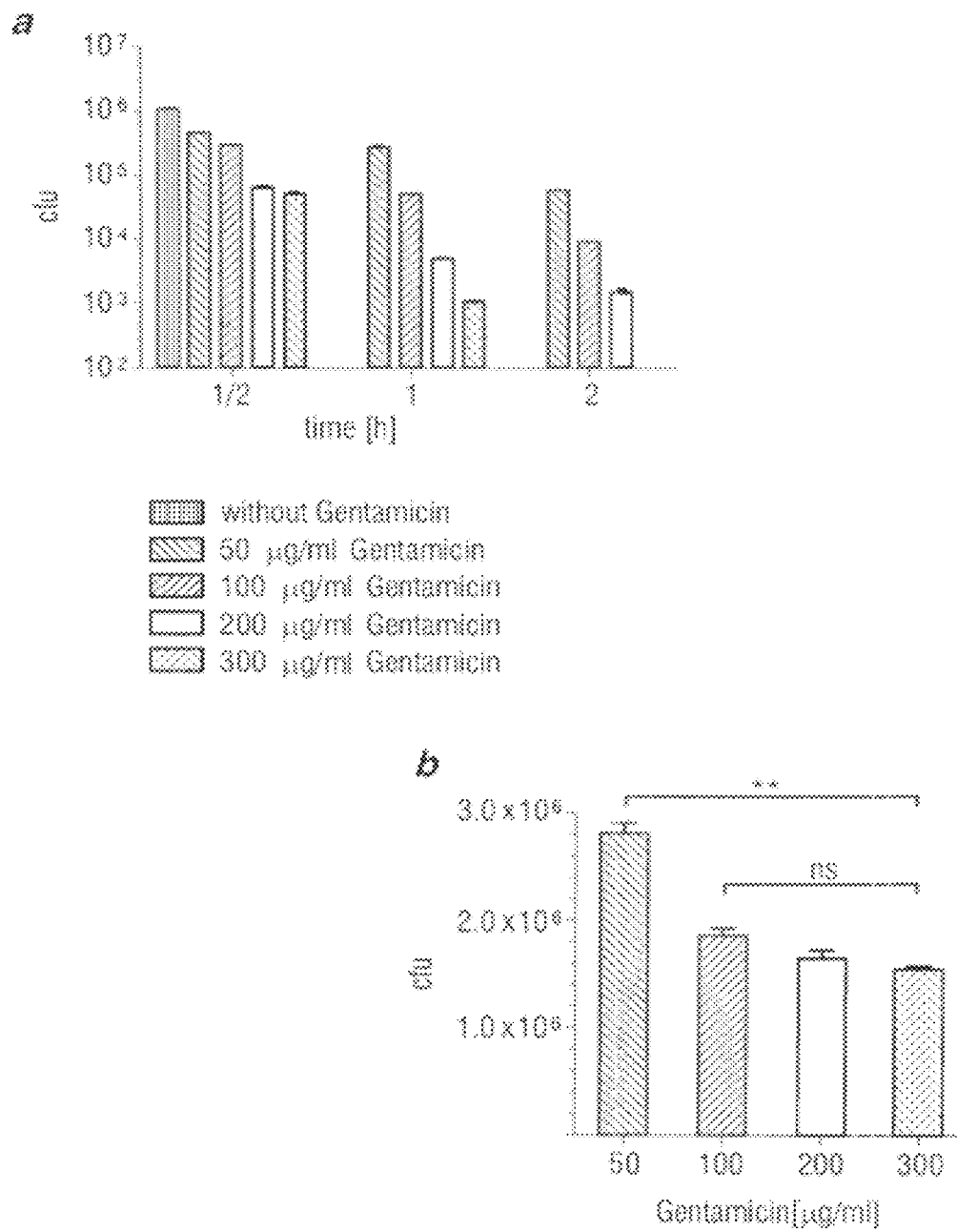

FIG. 12: Extracellular and intracellular activity of gentamicin against *S. typhimurium* delta-aroA. (a) $1\times10^6$ *S. typhimurium* delta-aroA were treated for ½ h, 1 h and 2 h with 50, 100, 200 and 300 µg/ml gentamicin and cfu was determined by serial dilution. (b) J774A.1 macrophages were infected with $1\times10^6$ *S. typhimurium* delta-aroA (logarithmic growth phase). Bacteria were washed 3 times with DMEM medium and centrifuged for 10 min at 4000 rpm (4° C.). After 1 h infection, cells were incubated for 1 h with 50, 100, 200 and 300 µg/ml gentamicin followed by a 1 h incubation with 10 µg/ml gentamicin. Cfu was determined after cell lysis by serial dilution. To avoid re-infection of cells during MACS separation and to assess the number of extracellular bacteria, extracellular bacteria have to be killed or substantially reduced during an incubation time of 1 hour. As depicted in (a), a 1 hour incubation with 50, 100 or 200 µg/ml gentamicin led to a 3 fold, 10 fold or 100 fold reduction of the cfu compared to control. In contrast, incubation with 300 µg/ml reduced free bacteria >1000 fold after 1 hour incubation and fully eliminated the bacteria after 2 hours. To determine the activity of these concentrations on intracellular bacteria, a similar protocol as used for cell separation was employed (b). Doses between 100-300 µg/ml gentamicin showed a slightly, 1.5 fold, increased activity compared to the 50 µg dose which is marginally active on extracellular bacteria with these short incubation time. In between the doses of 100-300 µg/ml gentamicin, there is no significant difference on intracellular cfu. Therefore, the highest dose of 300 µg/ml gentamicin was chosen for future experiments which will lead to >1000 fold reduction of extracellular bacteria in the experimental setting employed for cell separation.

Figure 13:
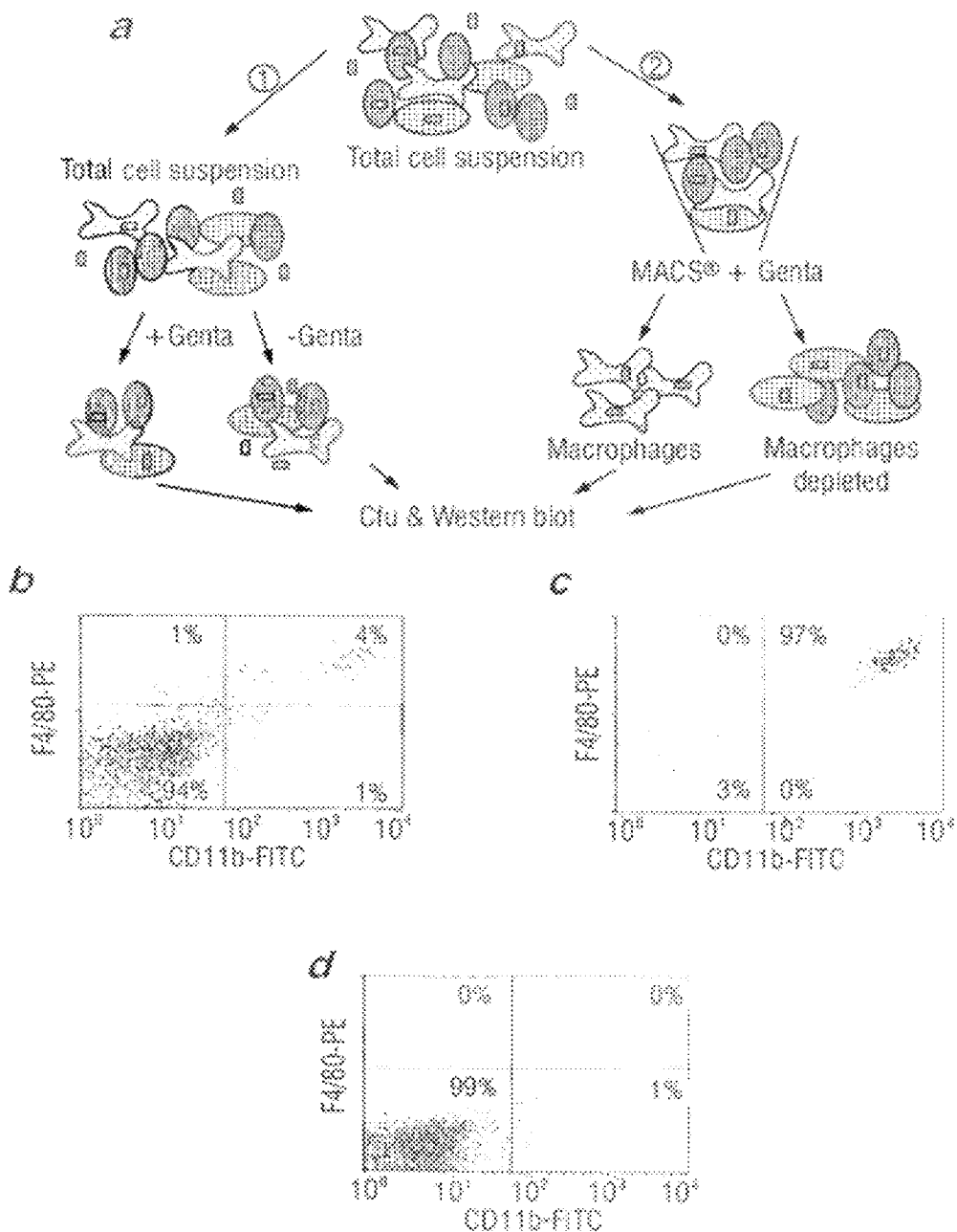

FIG. 13: Experimental schedule of cell separation. (a) After tumor removal and separating the total tumor cells (b) by 0.001% DNAse and 2 µg/ml dispase treatment, one part of the total tumor cells (1) was treated with or without 300 µg/ml gentamicin for 1 h. After the treatment cells were analysed for cfu and caspase-1 activation. The preparation treated with gentamycin consists mainly of intracellular bacteria, whereas the untreated preparation contains extra- and intracellular bacteria. The second part of total tumor cells (2) was labeled by an anti-F4/80 (IgG) antibody. Then a second anti-IgG antibody labeled with magnetic beads was added. Separating was performed using MACS columns in magnetic fields and results in two cell fractions: a macrophages fraction and a fraction of macrophages depleted. The purity of the macrophages fraction is between 96-99% (n=7). With these fractions, which were incubated with 300 µg/ml gentamicin throughout the procedure to prevent re-infection of cells by free bacteria, also the cfu and caspase-1 processing was assessed. Note that the macrophage fraction (c) contains a substantially lower amount of cells compared to the macrophage depleted (d) fraction. For cfu counts, normalization was performed after plating (cfu/cell number, infected cells/cell number), for Western Blotting, equivalent cell numbers were loaded.

Figure 14:
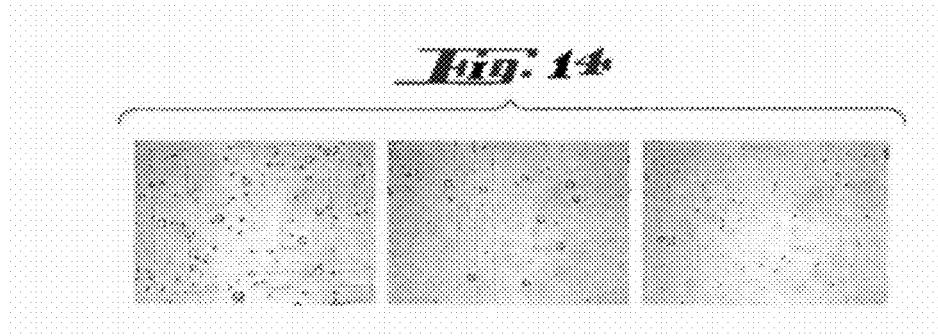

FIG. 14: Light microscopy (×100) of the three cell fractions after cell separation. To evaluate the efficacy of the cell separation which could influence the results with respect to the number of infected cells, light microscopy of the three different cell fractions was performed. The left panel shows the total tumor cell fraction. In the middle there are the separated macrophages. The left panel shows the macrophages depleted fraction. The cells of all cell fractions mainly appear as single cells.

FIG. 15: In vivo infection of tumor bearing Balb/c mice with $1\times10^6$ *Salmonella typhimurium* delta-aroA. Determination of cfu (a) and the number of infected cells (b) by L-Top agar assay after 6 h. Tumor-bearing Balb/c mice (n=4) were infected with *Salmonella typhimurium* delta-aroA ($1\times10^6$). After 6 h post infection spleens and tumors were removed, and cells were separated. Total cfu was determined by serial dilutions of lysed cells and the number of infected cells was determined by plating serial dilutions of intact cells in L-Top agar.

FIG. 16: In vivo infection of tumor-bearing Balb/c mice with $1\times10^6$ *S. flexneri* M90Tdelta-aroA. Determination of cfu (a, b) and the number of infected cells (c, d) by L-Top agar assay after 4 h, 6 h and 7 d. Tumor-bearing Balb/c mice (n=4) were infected with *S. flexneri* M90Tdelta-aroA ($1\times10^6$). After 4 h, 6 h and 7 d post infection spleens and tumors were removed, and cells were separated. Total cfu was determined by serial dilutions of lysed cells and the number of infected cells was determined by plating serial dilutions of intact cells in L-Top agar.

FIG. 17: In vivo infection of tumor bearing MMTV-Her2/new FVB mice with $1\times10^6$ *Salmonella typhimurium* delta-aroA. Determination of cfu (a, b) and the number of infected cells (c, d) by L-top agar assay after 6 h. Tumor-bearing MMTV-Her2/new FVB mice (n=4) were infected with *Salmonella typhimurium* delta-aroA ($1\times10^6$). After 6 h post infection spleens and tumors were removed, and cells were separated. Total cfu was determined by serial dilutions of lysed cells and the number of infected cells was determined by plating serial dilutions of intact cells in L-Top agar. The relative percentage of macrophages (e) 7d post infection in infected and non infected animals was determined by FACS-analysis. Similar to the results obtained with transplanted tumors, Salmonella infected TAMs with approx. 100 fold higher efficiency as compared to macrophages depleted tumor cells in a transgenic animal model bearing spontaneous breast adenocarcinoma (a-d). Also in this model, the majority of bacteria was intracellular. Salmonella treatment did not result in a measurable reduction of macrophage numbers in the tumors 7 days after infection.

FIG. 18: M90T, M90Tdelta-aroA and BS176delta-aroA induce Caspase-1 processing and apoptosis in macrophages isolated from spontaneous breast adenocarcinomas from transgenic mice ex vivo. Ex vivo infection of the three different cell fraction after cell isolation from Balb/c (a, b) and MMTV-Her2 (c, d) with *S. flexneri* M90T, *S. flexneri* M90Tdelta-aroA and *S. flexneri* BS176delta-aroA at a MOI of 100:1 for 1 h. After an incubation of 1 h with 300 µg/ml gentamicin the different probes were prepared for western blot. The antibody detects the procaspase-1 (45 kDa) and the activated caspase-1 20 kDa subunit. Note that the macrophage depleted fraction does not contain procaspase-1 in detectable levels. The PARP antibody detects the cleaved PARP fragment of 85 kDa.

FIG. 19: M90Tdelta-aroA predominantly resides in macrophages of tumors of transgenic mice bearing spontaneous breast adenocarcinoma and substantially reduce macrophage numbers 7 days after infection. Determination of cfu (a, c)

and the number of infected cells (b, d) by L-Top agar assay after 7 d. MMTV-Her2/new FVB mice (n=4) were infected with *S. flexneri* M90Tdelta-aroA and BS176delta-aroA (1×10$^6$). After 7 d post infection spleens and tumors were removed, and cells were separated. Total cfu was determined by serial dilutions of lysed cells and the number of infected cells was determined by plating serial dilutions of intact cells in L-Top agar. The relative percentage of macrophages (e) 7 d post infection in infected and non infected animals was determined by FACS-analysis. *S. flexneri* M90Tdelta-aroA still infects predominantly the TAMs 7 d post infection. We also determined the percentage of macrophages (e) 7 d post infection by FACS-analysis. There was a significant difference in the amount of macrophages in comparison to mice infected with BS176delta-aroA after 7 d. p<0.005. 7 days after i.v. infection, M90Tdelta-aroA predominantly resides within macrophages of spontaneous tumors (5 fold difference compared to macrophages depleted fractions). The non-invasive BS176delta-aroA strain is still present in the tumors with very low cell numbers and also found predominantly in macrophages. In contrast to *salmonella*, macrophage numbers are substantially decreased >4 fold (***: p<0.005) in tumors of mice infected with the infective M90Tdelta-aroA strain capable of inducing caspase-1 processing and apoptosis in comparison to the non-virulent BS176delta-aroA strain.

FIG. 20: Infection of tumor-bearing MMTV-Her2/new FVB mice with M90Tdelta-aroA but not BS176delta-aroA induces caspase-1 processing and apoptosis in the macrophage fraction of tumors 6 h and 7 d after i.v. infection. I.v. infection of tumor-bearing MMTV-Her2 (n=4) with *S. flexneri* M90Tdelta-aroA and *S. flexneri* BS176delta-aroA (1×10$^6$). After 6 h and 7 d cell fractions were separated and analysed by Western Blot. The antibody detects the pro-caspase-1 (45 kDa) and the activated 20 kDa subunit. The anti-cleaved PARP antibody detects the cleaved PARP fragment of 85 kDa. I.v. infection of spontaneous tumor-bearing transgenic mice with M90Tdelta-aroA resulted in a substantial induction of caspase-1 processing and apoptosis 6 h after infection. In contrast to salmonella, the pro-apoptotic activity persisted at day 7. Similar to the results observed in animals with transplanted tumors, no caspase-1 induction was measurable in the total tumor cell fraction of mice infected with M90Tdelta-aroA 7 days after infection, which might be explained by the substantial reduction of macrophages in these tumors.

FIG. 21: M90Tdelta-aroA predominantly targets TAMs isolated from human ascites cells ex vivo. The ascites cells consist of two different cell populations, on the one hand there are adherent cells and on the other cells there are suspensions cells. The two cell populations (a, b) were treated as separated cell types. Ex vivo infection was performed for the three different cell fraction after cell isolation from a patient and RAW 264.7 macrophages as a control with wt *S. flexneri* M907, *S. flexneri* M90Tdelta-aroA and *S. flexneri* BS176delta-aroA at a MOI of 100:1 for 1 h. After an incubation of 1 h with 300 µg/ml gentamicin serial dilutions were plated on BHI-agar. Next day cfu was determined. All results shown are mean±SD; ***: p<0.001, students t-test.

FIG. 22: Graphical scheme of the pMOhlipa plasmid.

FIG. 23: Determination of IpaB secretion by *E. coli* pMOhlipa. RAW 264.7 macrophages infected by M90T (positive, IpaB 64 kDa) and by BS176 (negative) were used as controls. IpaB secretion by *E. coli* pMOhlipa was detected by a 70 kDa product because HlyA signal sequence was fused to IpaB.

FIG. 24: Western Blot analysis for caspase-1 activation by *E. coli* in vitro. RAW 264.7 macrophages were infected for 3 h and 6 h by different *E. coli* DH5α strains (stationary growth phase). Infection of RAW 264.7 macrophages by *Shigella flexneri* M90T (mid-logarithmic growth phase) and treatment with staurosporine (4 µM) for 3 h was taken as positive control for caspase-1 activation. GAPDH was used as loading control.

FIG. 25: Western Blot analysis for caspase-1 activation in splenic tissue in vivo. In vivo infection of tumor-bearing Balb/c mice with 1×10$^6$ *E. coli* pMOhlipa, spleen cell isolation and Western Blot analysis for caspase-1 activation were performed. TAMs isolated from Balb/c mice were infected by M90T and taken as positive control for caspase-1 activation. GAPDH was used as loading control.

FIG. 26: Graphical scheme of plasmid pSPR17.

The contents of all cited references and patents are hereby incorporated by reference. The invention is explained in more detail by means of the following examples without, however, being restricted thereto.

DESCRIPTION OF THE INVENTION

The present invention has the object to provide novel tumor vaccines by means of which tumor-associated macrophages (TAM) are partially or completely depleted and an efficient tumor therapy can be achieved.

The object of the present invention has been surprisingly solved in one aspect by providing a non-pathogenic and/or attenuated bacterium which is capable of inducing apoptosis in macrophages.

In a preferred embodiment, above bacterium is capable of infecting macrophages.

In another preferred embodiment, such bacterium is selected from the group consisting of: gram-negative bacterium, gram-positive bacterium.

In a further preferred embodiment, such bacterium is selected from the group consisting of: *Shigella* spp., *Salmonella* spp., *Listeria* spp., *Mycobacterium* spp., *Escherichia* spp., *Yersinia* spp., *Vibrio* spp., *Pseudomonas* spp.

In a further preferred embodiment, such bacterium is selected from the group consisting of: *Shigella flexneri*, *Salmonella typhimurium*, *Mycobacterium bovis* BCG, *Listeria monocytogenes*, *Escherichia coli*, *Salmonella typhi*, *Yersinia enterocolitica*, *Vibrio cholerae*.

In a preferred embodiment, the attenuation is caused by deletion or inactivation of at least one gene selected from the group consisting of: aroA, aro, asd, gal, pur, cya, crp, phoP/Q, omp.

In a preferred embodiment, the attenuation results in an auxotrophic bacterium.

In a yet further preferred embodiment, the macrophages are M1 macrophages and/or M2 macrophages and preferably are M2 macrophages.

In a yet further preferred embodiment, the induction of apoptosis is achieved by caspase activation, preferably caspase-1 activation.

In another preferred embodiment, the bacterium is recombinant.

In another preferred embodiment, the bacterium carries at least one chromosomally integrated DNA, preferably recombinant DNA, encoding at least one protein selected from the group of: IpaB, SipB.

In another preferred embodiment, the bacterium carries at least one chromosomally integrated regulatory DNA, preferably recombinant DNA, leading to the constitutive expression of at least one protein selected from the group of: IpaB, SipB.

In another preferred embodiment, the bacterium carries at least one chromosomal deletion or inactivation of at least one regulatory DNA leading to the constitutive expression of at least one protein selected from the group of: IpaB, SipB.

In another preferred embodiment, the bacterium carries at least one plasmid, preferably recombinant plasmid.

In another preferred embodiment, the at least one plasmid, preferably recombinant plasmid, encodes at least one protein selected from the group of: IpaB, SipB.

In another preferred embodiment, the at least one plasmid, preferably recombinant plasmid, encodes at least one regulatory DNA leading to the constitutive expression of at least one protein selected from the group of: IpaB, SipB.

In another preferred embodiment, the non-pathogenic and/or attenuated bacterium is selected from the group consisting of: *Shigella flexneri* M90T delta-aroA, *Salmonella typhimurium* delta-aroA, *Shigella flexneri* BS176 delta-aroA pWR100.

In another aspect the object of the present invention has been surprisingly solved by providing a pharmaceutical composition comprising at least one bacterium, preferably at least one lyophilized bacterium, according to above aspects and embodiments and a pharmaceutically acceptable carrier.

In another aspect the object of the present invention has been surprisingly solved by providing a medicament comprising at least one non-pathogenic and/or attenuated bacterium according to above aspects and embodiments or a pharmaceutical composition according to above aspects and embodiments.

In another aspect the object of the present invention has been surprisingly solved by providing a medicament comprising at least one non-pathogenic and/or attenuated bacterium according to above aspects and embodiments or a pharmaceutical composition according to above aspects and embodiments for the treatment and/or prophylaxis of physiological and/or pathophysiological conditions selected from the group consisting of: diseases involving macrophage inflammations where macrophages are associated with disease onset or disease progression, tumor diseases, uncontrolled cell division, malignant tumors, benign tumors, solid tumors, sarcomas, carcinomas, hyperproliferative disorders, carcinoids, Ewing sarcomas, Kaposi sarcomas, brain tumors, tumors originating from the brain and/or the nervous system and/or the meninges, gliomas, neuroblastomas, stomach cancer, kidney cancer, kidney cell carcinomas, prostate cancer, prostate carcinomas, connective tissue tumors, soft tissue sarcomas, pancreas tumors, liver tumors, head tumors, neck tumors, oesophageal cancer, thyroid cancer, osteosarcomas, retinoblastomas, thymoma, testicular cancer, lung cancer, bronchial carcinomas, breast cancer, mamma carcinomas, intestinal cancer, colorectal tumors, colon carcinomas, rectum carcinomas, gynecological tumors, ovary tumors/ovarian tumors, uterine cancer, cervical cancer, cervix carcinomas, cancer of body of uterus, corpus carcinomas, endometrial carcinomas, urinary bladder cancer, bladder cancer, skin cancer, basaliomas, spinaliomas, melanomas, intraocular melanomas, leukemia, chronic leukemia, acute leukemia, lymphomas, infection, viral or bacterial infection, influenza, chronic inflammation, organ rejection, autoimmune diseases, diabetes and/or diabetes type II.

In another aspect the object of the present invention has been surprisingly solved by providing a medicament comprising at least one non-pathogenic and/or attenuated bacterium according to above aspects and embodiments or a pharmaceutical composition according to above aspects and embodiments for the treatment and/or prophylaxis of physiological and/or pathophysiological conditions selected from the group consisting of: diseases involving macrophage inflammations where macrophages are associated with disease onset or disease progression, tumor diseases, uncontrolled cell division, malignant tumors, benign tumors, solid tumors, sarcomas, carcinomas, hyperproliferative disorders, carcinoids, Ewing sarcomas, Kaposi sarcomas, brain tumors, tumors originating from the brain and/or the nervous system and/or the meninges, gliomas, neuroblastomas, stomach cancer, kidney cancer, kidney cell carcinomas, prostate cancer, prostate carcinomas, connective tissue tumors, soft tissue sarcomas, pancreas tumors, liver tumors, head tumors, neck tumors, oesophageal cancer, thyroid cancer, osteosarcomas, retinoblastomas, thymoma, testicular cancer, lung cancer, bronchial carcinomas, breast cancer, mamma carcinomas, intestinal cancer, colorectal tumors, colon carcinomas, rectum carcinomas, gynecological tumors, ovary tumors/ovarian tumors, uterine cancer, cervical cancer, cervix carcinomas, cancer of body of uterus, corpus carcinomas, endometrial carcinomas, urinary bladder cancer, bladder cancer, skin cancer, basaliomas, spinaliomas, melanomas, intraocular melanomas, leukemia, chronic leukemia, acute leukemia, lymphomas, infection, viral or bacterial infection, influenza, chronic inflammation, organ rejection, autoimmune diseases, diabetes and/or diabetes type II, whereby
  (a) apoptosis is induced in tumor-associated macrophages (TAM) and tumor-associated macrophages (TAM) are partially or completely depleted and/or
  (b) apoptosis is induced in disease-associated macrophages and disease associated macrophages are partially or completely depleted.

In another aspect the object of the present invention has been surprisingly solved by providing the use of a medicament according to above aspects and embodiments for the treatment and/or prophylaxis of physiological and/or pathophysiological conditions according to above aspects and embodiments, where the medicament is administered before and/or during and/or after the treatment with at least one further pharmacologically active substance.

In a preferred embodiment, the further pharmacologically active substance is selected from the group consisting of: DNA topoisomerase I and/or II inhibitors, DNA intercalators, alkylating agents, microtubuli destabilizers, hormone and/or growth factor receptor agonists and/or antagonists, inhibitors of signal transduction, antibodies against growth factors and their receptors, kinase inhibitors, antimetabolites.

In a further preferred embodiment, the further pharmacologically active substance is selected from the group consisting of: actinomycin D, aminoglutethimide, asparaginase, avastin, azathioprine, BCNU (carmustine), bleomycin, busulfan, carboplatin, CCNU (lomustine), chlorambucil, cisplatin, colaspase, cyclophosphamide, cytarabine, dactinomycin, daunorubicin, diethylstilbestrol, doxorubicin (adriamycin), DTIC (dacarbacin), epirubicin, erbitux, erythrohydroxynonyladenine, ethynyloestradiol, etoposide, fludarabine phosphate, fluoxymesterone, flutamide, gemcitabine, Gleevec/Glivec, Herceptin, hexamethylmelamine, hydroxyurea, hydroxyprogesterone caproate, idarubicin, ifosfamide, interferon, iressa, irinotecan, L-asparaginase, leucovorin, mechlorethamine, medroxyprogesterone acetate, megestrol acetate, melphalan, mesna, methotrexate, mitomycin C, mitotane, mitoxantrone, N-phosphonoacetyl-L-aspartate (PALA), oxaliplatin, pentostatin, plicamycin, prednisolone, prednisone, procarbazine, raloxifen, rapamycin, semustine, sorafenib, streptozocin, tamoxifen, tarceva, taxotere, teniposide, testosterone propionate, thioguanine, thiotepa, topotecan, trimethylmelamine, uridine, vinblastine, vincristine, vindesine, vinorelbine, 2',2'-difluorodeoxycytidine, 5-fluorodeoxyuridine monophosphate, 5-azacytidine cladribine, 5-fluorodeoxyuridine, 5-fluorouarcil (5-FU), 6-mercaptopurine.

In another aspect the object of the present invention has been surprisingly solved by providing the use of a medicament according to above aspects and embodiments for the treatment and/or prophylaxis of physiological and/or pathophysiological conditions according to above aspects and embodiments, where the medicament is administered before and/or during and/or after the treatment with radio-therapy and/or surgery.

In another aspect the object of the present invention has been surprisingly solved by providing a process for the production of a non-pathogenic and/or attenuated bacterium according to above aspects and embodiments comprising the following steps:
(a) deletion or inactivation of at least one gene selected from the group consisting of: aroA, aro, asd, gal, pur, cya, crp, phoP/Q, omp in a non-pathogenic and/or non-attenuated bacterium; and/or
(b) integration of DNA, preferably recombinant DNA, into the genome of such non-pathogenic and/or attenuated bacterium, comprising DNA which encodes at least one protein selected from the group of: IpaB, SipB; and/or
(c) introduction of at least one plasmid, preferably recombinant plasmid, into such non-pathogenic and/or attenuated bacterium, comprising DNA which encodes at least one protein selected from the group of: IpaB, SipB; and/or
(d) integration of DNA, preferably recombinant DNA, into the genome of such non-pathogenic and/or attenuated bacterium, comprising at least one regulatory DNA which enables the constitutive expression of at least one protein selected from the group of: IpaB, SipB; and/or
(e) chromosomal deletion or inactivation of at least one regulatory DNA which leads to the constitutive expression of at least one protein selected from the group of: IpaB, SipB; and/or
(f) introduction of at least one plasmid, preferably recombinant plasmid, into such non-pathogenic and/or attenuated bacterium, comprising at least one regulatory DNA which enables the constitutive expression of at least one protein selected from the group of: IpaB, SipB.

In another aspect the object of the present invention has been surprisingly solved by providing a pharmaceutical kit comprising at least one non-pathogenic and/or attenuated bacterium according to above aspects and embodiments or a pharmaceutical composition according to above aspects and embodiments or a medicament according to above aspects and embodiments and a pharmacologically acceptable buffer for i.v. injection.

In another aspect the object of the present invention has been surprisingly solved by providing a method of treating a mammal, preferably a human, suffering from a disease comprising the administration of at least one non-pathogenic and/or attenuated bacterium according to above aspects and embodiments or a pharmaceutical composition according to above aspects and embodiments or a medicament according to above aspects and embodiments to that mammal, preferably human, whereby
(a) apoptosis is induced in tumor-associated macrophages (TAM) and tumor-associated macrophages (TAM) are partially or completely depleted and/or
(b) apoptosis is induced in disease-associated macrophages and disease associated macrophages are partially or completely depleted.

In a preferred embodiment, the disease is selected from the group consisting of: diseases involving macrophage inflammations where macrophages are associated with disease onset or disease progression, tumor diseases, uncontrolled cell division, malignant tumors, benign tumors, solid tumors, sarcomas, carcinomas, hyperproliferative disorders, carcinoids, Ewing sarcomas, Kaposi sarcomas, brain tumors, tumors originating from the brain and/or the nervous system and/or the meninges, gliomas, neuroblastomas, stomach cancer, kidney cancer, kidney cell carcinomas, prostate cancer, prostate carcinomas, connective tissue tumors, soft tissue sarcomas, pancreas tumors, liver tumors, head tumors, neck tumors, oesophageal cancer, thyroid cancer, osteosarcomas, retinoblastomas, thymoma, testicular cancer, lung cancer, bronchial carcinomas, breast cancer, mamma carcinomas, intestinal cancer, colorectal tumors, colon carcinomas, rectum carcinomas, gynecological tumors, ovary tumors/ovarian tumors, uterine cancer, cervical cancer, cervix carcinomas, cancer of body of uterus, corpus carcinomas, endometrial carcinomas, urinary bladder cancer, bladder cancer, skin cancer, basaliomas, spinaliomas, melanomas, intraocular melanomas, leukemia, chronic leukemia, acute leukemia, lymphomas, infection, viral or bacterial infection, influenza, chronic inflammation, organ rejection, autoimmune diseases, diabetes and/or diabetes type II.

Definitions

In the course of the invention, the term "infecting macrophages" in connection with a bacterium refers to a bacterium, which invades or enters macrophages and becomes an intracellular component of such macrophages analogous to viral infections of cells.

The term "inducing apoptosis in macrophages" in connection with a bacterium in the course of the invention refers to a bacterium, which induces programmed cell death (apoptosis) in such macrophages so that such macrophages commit suicide and die.

The terms "M1 macrophage" or "M1 type macrophage" or "M1 type polarized macrophage" in the course of the present invention refer to macrophages that are usually not present at the tumor site (Sica A et al., Eur. J. Cancer 2006, 42: 717-727).

The terms "M2 macrophage" or "M2 type macrophage" or "M2 type polarized macrophage" in the course of the present invention refer to macrophages that are usually present at the tumor site and include M2a, M2b and M2c subpopulations (Sica A et al., Eur. J. Cancer 2006, 42: 717-727). Such macrophages can be, but do not necessarily have to be tumor-associated macrophages (TAM). Most likely, TAM represent a skewed M2 population.

In the course of the invention the term "tumor-associated macrophage (TAM)" refers to $F4/80^+$ $CD11b^+$ macrophages residing in a tumor.

In the course of the invention the term "auxotrophic bacterium" refers to a bacterium carrying at least one mutation which leads to a reduced growth rate in the infected host.

In the course of the invention the term "attenuated bacterium" refers to a bacterium, which is attenuated in its virulence either by a loss of function in at least one virulence factor necessary for infection of the host and/or by an auxotrophic mutation leading to an impaired growth within the host, i.e. the virulence is reduced compared to the non-attenuated wild-type counterpart, for instance a bacterium that carries a deleted or inactivated aroA, aro, asd, gal, pur, cya, crp, phoP/Q, omp gene or is a temperature-sensitive mutant or an antibiotic-dependent mutant (Cardenas L. and Clements J. D. Clin Microbiol Rev 1992; 5: 328-342).

The term "recombinant DNA" in the course of the present invention refers to artificial DNA which is molecular-genetically engineered through the combination or insertion or deletion of one or more (parts of) DNA strands, thereby combining DNA sequences which would not normally occur together in nature. In terms of genetic modification, recombinant DNA is produced through the addition of relevant DNA into an existing organismal genome or deletion of relevant DNA in an existing organismal genome, such as the chromosome and/or plasmids of bacteria, to code for or alter different traits for a specific purpose, such as immunity. It differs from genetic recombination, in that it does not occur through processes within the cell or ribosome, but is exclusively molecular-genetically engineered.

The term "recombinant plasmid" in the course of the present invention refers to recombinant DNA which is present in the form of a plasmid.

The term "recombinant bacterium" in the course of the present invention refers to a bacterium harboring recombinant DNA and/or recombinant plasmid(s) and/or non-recombinant DNA artificially introduced into such bacterium.

The term "nucleotide sequence" in the course of the present invention refers to dsDNA, ssDNA, dsRNA, ssRNA or dsDNA/RNA hybrids. Preferred is dsDNA.

The term "epigenetic changes" in the course of the present invention refers to changes on the DNA level, i.e. by DNA methylation or demethylation, binding polycomb proteins, histone acylation etc. which influence the expression level of at least one gene.

The term "regulatory DNA" in the course of the present invention refers to regions in the DNA which influence the expression of at least one gene by binding of regulatory proteins or by inducing epigenetic changes.

The term "spp." in connection with any bacterium is intended to comprise for the purpose of the present invention all members of a given genus, including species, subspecies and others. The term "*Salmonella* spp." for instance is intended to comprise all members of the genus *Salmonella*, such as *Salmonella typhi* and *Salmonella typhimurium*.

The term "non-pathogenic" in connection with "bacterium" in the course of the present invention refers to a bacterium which does not cause a disease or disease conditions in a host.

Bacterial infections comprise, but are not limited to, anthrax, bacterial meningitis, botulism, brucellosis, campylobacteriosis, cat scratch disease, cholera, diphtheria, epidemic typhus, impetigo, legionellosis, leprosy (Hansen's disease), leptospirosis, listeriosis, lyme disease, melioidosis, MRSA infection, nocardiosis, pertussis (whooping cough), plague, pneumococcal pneumonia, psittacosis, Q fever, Rocky Mountain Spotted Fever (RMSF), salmonellosis, scarlet fever, shigellosis, syphilis, tetanus, trachoma, tuberculosis, tularemia, typhoid fever, typhus, urinary tract infections, bacterially caused heart diseases.

Viral infections comprise, but are not limited to, AIDS, AIDS related complex (ARC), chickenpox (varicella), common cold, cytomegalovirus infection, Colorado tick fever, Dengue fever, Ebola haemorrhagic fever, hand, foot and mouth disease, hepatitis, Herpes simplex, Herpes zoster, HPV, influenza (flu), Lassa fever, measles, Marburg haemorrhagic fever, infectious mononucleosis, mumps, poliomyelitis, progressive multifocal leukencephalopathy, rabies, rubella, SARS, smallpox (variola), viral encephalitis, viral gastroenteritis, viral meningitis, viral pneumonia, West Nile disease, Yellow fever.

Chronic inflammations or chronic inflammatory diseases comprise, but are not limited to, chronic cholecystitis, bronchiectasis, rheumatoid arthritis, Hashimoto's thyroiditis, inflammatory bowel disease (ulcerative colitis and Crohn's disease), silicosis and other pneumoconiosis.

Autoimmune diseases comprise, but are not limited to, systemic syndromes, such as SLE, Sjögren's syndrome, scleroderma, rheumatoid arthritis and polymyositis as well as local syndromes, such as IDDM, Hashimoto's thyroiditis, Addison's disease, pemphigus vulgaris, psoriasis, atopic dermatitis, atopic syndrome, asthma, autoimmune haemolytic anaemia, multiple sclerosis.

The above illustrated bacteria as well as the preferred embodiments are herein referred to as bacterium of the invention.

The bacterium of the invention is advantageously suited for use in tumor therapy, as live vaccines in the course of tumor-targeting. That is by means of the bacterium of the invention, apoptosis is induced in tumor-associated macrophages (TAM) which are partially or completely depleted. Thereby, the tumor is exposed and can be attacked by means of conventional anti-tumor drugs.

The bacterium of the invention is advantageously suited for use in therapy of chronic inflammatory disease associated by macrophage inflammation, as live therapeutic. That is by means of the bacterium of the invention, apoptosis is induced in macrophages associated with the disease and these macrophages are partially or completely depleted from the site of inflammation. Thereby, one factor responsible for sustained inflammation is missing and the chronic inflammation can regress. Examples for such diseases are benign proliferative diseases associated with inflammation like benign prostatic hyperplasia or chronic inflammatory autoimmune diseases like Morbus Crohn, inflammatory bowel disease, rheumatoid arthritis, asthma.

The non-pathogenic and/or attenuated bacteria of the present invention can be administered in a known manner. The route of administration may thereby be any route which effectively transports the bacteria to the appropriate or desired site of action, for example non-orally or orally, in particular intravenously, topically, transdermally, pulmonary, rectally, intravaginally, nasally or parenteral or by implantation. Intravenous administration is preferred.

Non-oral administration can take place for example by intravenous, subcutaneous, intramuscular injection of sterile aqueous or oily solutions, suspensions or emulsions, by means of implants or by ointments, creams or suppositories. Administration as sustained release form is also possible where appropriate. Implants may comprise inert materials, e.g. biodegradable polymers or synthetic silicones such as, for example, silicone rubber. Intravaginal administration is possible for example by means of vaginal rings. Intrauterine administration is possible for example by means of diaphragms or other suitable intrauterine devices. Transdermal administration is additionally provided, in particular by means of a formulation suitable for this purpose and/or suitable means such as, for example, patches.

Oral administration can take place for example in solid form as tablet, capsule, gel capsule, coated tablet, granulation or powder, but also in the form of a drinkable solution. The compounds of the invention can for oral administration be combined with known and ordinarily used, physiologically tolerated excipients and carriers such as, for example, gum arabic, talc, starch, sugars such as, for example, mannitol, methylcellulose, lactose, gelatin, surface-active agents, magnesium stearate, cyclodextrins, aqueous or nonaqueous carriers, diluents, dispersants, emulsifiers, lubricants, preservatives and flavorings (e.g. essential oils). The bacteria of the invention can also be dispersed in a microparticulate, e.g. nanoparticulate, composition.

Possible modes of manufacturing of the non-pathogenic and/or attenuated bacteria of the invention are:

(A) A virulent bacterial strain, preferably a *Salmonella* strain is attenuated, preferably auxotrophic, by mutagenesis, selection, and/or targeted genomic modification. The attenuated bacterial strain, preferably *Salmonella* strain, can be treated as follows:

(i) genomic deletion of negative regulatory DNA leading to constitutive SipB/IpaB expression, if necessary, combined with additional DNA manipulations to ensure the expression of additional elements necessary for apoptosis induction in macrophages (invasions, secretory system, transport system)

(ii) genomic or plasmid insertion of positive regulatory DNA leading to constitutive SipB/IpaB expression, if necessary, combined with additional DNA manipulations to ensure the expression of additional elements necessary for apoptosis induction in macrophages (invasions, secretory system, transport system)

(iii) genomic or plasmid insertion of DNA encoding SipB/IpaB which are constitutively expressed, if necessary, combined with additional DNA manipulations to ensure the expression of additional elements necessary for apoptosis induction in macrophages (invasions, type III transport system)

(B) A virulent intracellular pathogenic bacterium, such as *Listeria* or *Shigella*, is attenuated, preferably auxotrophic, by mutagenesis, selection, and targeted genomic modification. The attenuated bacterium is treated as follows:

(i) genomic or plasmid insertion of DNA encoding SipB/IpaB which are constitutively expressed, if necessary, combined with additional DNA manipulations to ensure the expression of additional elements necessary for apoptosis induction in macrophages (invasions, type III transport system)

(C) An avirulent *Shigella* strain is attenuated, preferably auxotrophic, by mutagenesis, selection, and targeted genomic modification. The attenuated *Shigella* is treated as follows:

(i) genomic or plasmid insertion of DNA encoding SipB/IpaB which are constitutively expressed, if necessary, combined with additional DNA manipulations to ensure the expression of additional elements necessary for apoptosis induction in macrophages (invasions, type III transport system)

(D) An non-pathogenic or extracellular pathogenic bacterium (such as *E. coli*, Vibrio) is attenuated, preferably auxotrophic, by mutagenesis, selection, and targeted genomic modification. The attenuated bacterium is treated as follows:

(i) genomic or plasmid insertion of DNA encoding SipB/IpaB which are constitutively expressed, if necessary, combined with additional DNA manipulations to ensure the expression of additional elements necessary for apoptosis induction in macrophages (invasions, type III transport system)

EXAMPLES

Example 1

Methods

Plasmids. *Escherichia coli* strains carrying plasmids pKD3, pKD4 (Datsenko, K. A. & Wanner, B. L. Proc Natl Acad Sci U S A 2000, 97: 6640-6645), and pCP20 (Cherepanov, P. P. & Wackernagel, W. Gene 1995, 158: 9-14) were obtained from the Department of Biotechnology, University of Wuerzburg. The plasmids pKD3 and pKD4 are π dependent and carry chloramphenicol and kanamycin resistance genes, respectively, flanked by FLP recombinase recognition sites (FRT sites). The pCP20 plasmid contains a temperature sensitive replicon and the yeast FLP recombinase transcribed from the IpR promoter under the control of the I cI857 repressor (Cherepanov, P. P. & Wackernagel, W. Gene 1995, 158: 9-14).

Media, Chemicals and Other Reagents. Ampicillin-, chloramphenicol- (CmR), and kanamycin-resistant (KmR) transformants were selected on trypticase soy agar (1.2% agar) (TSA) (Difco Laboratories) containing the respective antibiotic at 100, 25, and 30 µg/ml. A total of 1 mM L-arabinose (Sigma) was used. Oligonucleotides were from MWG. Enzymes were from Fermentas unless indicated otherwise. Taq polymerase was used in all PCR tests. Taq (Biotherm, Genecraft) polymerases were used according to the manufacturers instructions to generate DNAs for cloning and mutagenesis. Qiagen products (Hilden, Germany) were used to isolate plasmid DNAs, gel-purify fragments, or purify PCR products.

Bacterial strains, growth conditions and genetic procedures The strain *S. typhimurium* delta-aroA used harbours a plasmid based kanamycin resistance (plasmid pToIC$_{Kan}$, Hotz et al., unpublished data). Plasmid stability is 100% in vivo and thus use of this strain allowed selection on kanamycin (data not shown). The *S. flexneri* 5a strains used are the wt M90T [streptomycin (Sm) resistant] (Allaoui, A., Mounier, J., Prevost, M. C., Sansonetti, P. J. & Parsot, C. Mol Microbiol 1992, 6: 1605-1616) and its noninvasive variant BS176 (lacking the virulence plasmid pWR100) (Sansonetti, P. J., Kopecko, D. J. & Formal, S. B. Infect Immun 1982, 35: 852-860; Buchrieser, C. et al. Mol Microbiol 2000, 38: 760-7) from the university Sophia-Antipolis of Nice. All strains were routinely grown on trypticase soy broth (TSB) (Becton Dickinson and Co.), trypticase soy agar (12% agar) (TSA) (Difco Laboratories), Luria-Bertani broth (LB) (Miller, J. H. A short course in Bacterial Genetics, Cold Spring Harbor Laboratory Press, Cold Spring Harbor, N.Y., 1992) or brain heart infusion (BHI). TSA containing 100 mg of Congo red dye (Cr) per liter was used to select Cr+ clones of *Shigella* spp. (Maurelli, A. T., Blackmon, B. & Curtiss, R., 3rd. Infect Immun 1984, 43 : 195-201). When necessary, Amp (100 µg/ml), Kan (25 µg/ml) or Cm (30 mg/ml) (all from Sigma Chemical) were added to bacterial cultures. Strains containing pCP20 were incubated at 30° C. unless otherwise noted below. Isolation of the 220 kb virulence plasmid pWR100 from M90T was performed by a large-construct kit (QIAGEN).

Linear DNA preparation. Linear DNA containing antibiotic resistance genes were prepared from pKD3 or pKD4 using the method described by Datsenko and Wanner (Datsenko, K. A. & Wanner, B. L. Proc Natl Acad Sci U S A 2000, 97: 6640-6645). Primers for PCR reactions were designed to contain 50 by of homology to the gene of interest as well as P1 and P2 sites used to prime from pKD3 or pKD4. Insert verification (below) was carried out using primers AroAup and aroAdown. PCR reactions were carried out using Taq polymerase according to the manufacturer's (Biotherm, Genecraft) recommendations.

PCR analysis was carried out by colony PCR. Briefly, colonies were resuspended in 50 µl of water and boiled for 10 min to make DNA lysates. Each lysate was assayed using the appropriate primer set by PCR. PCR reactions were carried out using Taq polymerase according to the manufacturer's recommendation (Biotherm, Genecraft). The following primers were used:

```
AroAup
                                           (SEQ ID NO: 1)
GGGGTTTTTATTTCTGTTGTAGAGAGTTGAGTTCATGGAATCGTG-

TAGGCTGGAGCTGCTTC

AroAdown
                                           (SEQ ID NO: 2)
GGCCGTGCATTTGGGATCAAGAATCGTCACTGGTGTATCTG-

CATATGAATATCCTCCTTA

AroAFr_up
                                           (SEQ ID NO: 3)
GATTTCTACCGCAATGACG

AroAFr_down
                                           (SEQ ID NO: 4)
GGAAACAAGTGAGCGTTTC C1
                                           (SEQ ID NO: 5)
TTATACGCAAGGCGACAAGG (Datsenko, K. A. & Wanner, B. L. Proc Natl Acad Sci USA 2000, 97: 6640-6645)

C2
                                           (SEQ ID NO: 6)
GATCTTCCGTCACAGGTAGG (Datsenko, K. A. & Wanner, B. L. Proc Natl Acad Sci USA 2000, 97: 6640-6645)

K1
                                           (SEQ ID NO: 7)
CAGTCATAGCCGAATAGCCT (Datsenko, K. A. & Wanner, B. L. Proc Natl Acad Sci USA 2000, 97: 6640-6645)

K2
                                           (SEQ ID NO: 8)
CGGTGCCCTGAATGAACTGC (Datsenko, K. A. & Wanner, B. L. Proc Natl Acad Sci USA 2000, 97: 6640-6645)
```

To create a strain which is attenuated in growth but not in its virulence we started with the engineered strain *Shigella flexneri* BS176delta-aroA. So the 200 kb virulence plasmid pWR100 of *Shigella flexneri* M90T was isolated by a large-construct kit (QIAGEN). After that this virulence plasmid and the helper plasmid pCP20, carrying an ampicilin-resistance, were transformed in the already constructed BS176delta-aroA strain. After this double transformation and incubation at 30° C. overnight the ampicilin-resistant colonies were screened for the virulence plasmid pWR100 (pWR100_up 5'-GATGCAGGCCAAGAGGTTAG-3' (SEQ ID NO:9); pWR100_down 5'-GCGTTGATGACCGCATC-3' (SEQ ID NO:10) and for the aroA-knockout (AroAFr_up 5'-GATTTCTACCGCAATGACG-3' (SEQ ID NO:11); AroAFr_down 5'-GGAAACAAGTGAGCGTTTC-3' (SEQ ID NO:12). This strain was termed *Shigella flexneri* M90Tdelta-aroA. The pCP20 plasmid containing a temperature sensitive replicon was cured by incubation overnight at 43° C.

HeLa cell invasion assays and survival assay. Gentamicin protection assays with HeLa cells were performed as previously described (Elsinghorst E A, 1994), with some minor modifications. HeLa-cell (ATCC CCL-2) monolayers were grown to semiconfluence in 75-$cm^2$ flasks in Dulbecco's Modified Eagle Medium (DMEM, Gibco) containing 10% fetal bovine serum (FBS, Gibco), 2 mM L-glutamine (Gibco), penicillin, and streptomycin (180 μg/ml for both, Gibco). One flask was trypsinized with 0.25% trypsin (Pan), and the concentration of cells was adjusted to $2\times10^5$ cells/ml in DMEM. Six-well plates were seeded with 2 ml of HeLa cells, which were grown overnight at 37° C. in 5% $CO_2$ to an approximate confluence of 90%. HeLa cells were washed, and the DMEM was changed 2 h before the addition of bacteria. Log-phase cultures of bacteria (grown in LB medium) were added at an estimated multiplicity of infection of 100. After the addition of bacteria plates were incubated at 37° C. in 5% $CO_2$ for 1 h. The plates were washed three times with D-phosphate buffer saline (Gibco) and then incubated with DMEM containing gentamicin (100 μg/ml) for 1 h at 37° C. in 5% $CO_2$. After certain timepoints HeLa cells were lysed in a 0.1% Triton X-100 solution for 10 min. The bacteria were plated on LB agar plates, and bacterial colonies were counted after growth at 37° C. for 18 h.

Intra- and intercellular growth assays. To study intracellular multiplication and behavior of cell-to-cell spreading, Giemsa staining of the cells was used initially. Briefly, HeLa-cells ($1\times10^5$) in 45-mm diameter tissue culture plates on coverslips (Ø20 mm) infected at a multiplicity of infection of 100:1 for one hour, were washed two times with 1× PBS and fixed for 5 to 7 min with methanol at room temperature. Plates were air dried and stained for 15 to 60 min with Giemsa dye (Sigma) prepared as described in the manufacturer's instructions. After the plates were washed three times with distilled water, they were air dried and observed under oil immersion. Time points of 1 h and 4 h post infection were examined.

L-Top agar assay. An L-Top agar assay was used to determine intercellular spreading. HeLa-cells ($7\times10^5$) in 6-well tissue culture plates were infected at a multiplicity of infection of 500:1 for one hour and were washed two times with 1× PBS. After that, infected cells were irradiated for 20 min at 20 Gray. Subsequently, uninfected HeLa-cells were incubated with the irradiated *shigella*-infected HeLa-cells in a ratio of 70:1 for 2 h, 8 h and 12 h. After 1 h incubation with 100 μg/ml gentamicin, the concentration of gentamicin was reduced to 10 μg/ml. At all timepoints serial dilutions made in SeaPlaque Agarose (Biozym Scientific GmbH, Oldendorf) were plated out on BHI agar plates. The agar plates were incubated overnight at 37° C. The number of bacterial colonies was determined by counting the spots. Every colony marked an infected HeLa-cell.

Mice. Six- to eight-week-old female mice were injected subcutaneously with either $1\times10^4$ murine 4T1 mammary cancer cells (ATCC: CRL-2539), $1\times10^6$ B78-D14 (Rymsa, B., Becker, H. D., Lauchart, W. & de Groot, H. Res Commun Chem Pathol Pharmacol 1990, 68: 263-266; Lode, H. N. et al. J Clin Invest 2000, 105: 1623-1630) melanoma cells and $1\times10^6$ P815-PSA (J Fensterle, J., Bergmann, B, Yone, CLRP, Hotz, C, Meyer, S R, Spreng, S, Goebel, W, Rapp, U R and I Gentschev. Cancer Gene Therapy 2007) mastocytoma cells each resuspended in 100 μl phosphate-buffered saline (PBS).

All procedures involving mice were conducted in accordance with the 'Regierung von Unterfranken' (Würzburg, Germany). Balb/c o1a HSD, C57/BL6, DBA-2 and MMTV-Her2/new FVB were ordered from Harlan Winkelmann GmbH (Borchen, Germany). All animals were housed at the Institut für Medizinische Strahlenkunde and Zellforschung (MSZ) animal care facility.

Histological and immunohistochemistrial analysis of tumors. 4T1-($1\times10^4$), B78-D14-($1\times10^6$) and P815-PSA-($1\times10^6$) cells were injected subcutaneously in Balb/c, C57/BL6 and DBA/2 mice. When tumors had been grown to 1.5-2 cm in diameter, they were aseptically excised. The tumors were formalin fixed, sectioned, and stained with hematoxylin and eosin.

To identify macrophages at the tumor site, tissues were fixed in 4% buffered paraformaldehyde for one day, paraffin embedded, and processed for sectioning. Subsequently sections were immunostained using the pan-macrophage anti-F4/80 rat monoclonal antibody (Acris Antibodies GmbH) and specific reactivity was detected using a peroxidase-based detection kit (Vector Laboratories) as described (Gouon-Evans, V., Rothenberg, M. E. & Pollard, J. W. Development 2000, 127: 2269-2282). An anti-CD45 antibody (BD Pharmingen) and the peroxidase-based detection kit (Vector Laboratories) was also used to examine the grade of inflammation.

I.v. infection of tumor-bearing mice. Bacteria were harvested at mid-logarithmic phase (*Shigella*) or stationary phase (*Salmonella*), washed in 1× PBS three times, and diluted with 1× PBS prior to injection. 100 µl of the suspension were injected into the lateral tail vein of 4T1 tumor-bearing Balb/c mice 14 days post cell implantation, or into 0.5 year old tumor-bearing female MMTV-Her2 mice. To determine bacterial load in tumor and spleen tissues, mice were sacrificed, the organs were excised, weighed and homogenized with 70 µm and 40 µm cell strainer. Cell numbers of every cell fraction were counted and cfu or the number of infected cells was determined.

Determination of cfu and infected cell number. In order to determine the number of colony forming units serial dilutions in 1× PBS containing 0.1% Triton-X (Roth) were plated out on LB agar plates. For experiments with *Salmonella typhimurium* delta-aroA pToIC$_{Kan}$ LB agar plates containing 25 µg/ml Kanamycin were used. The agar plates were incubated overnight at 37° C. upside-down. The number of bacterial colonies was determined by counting the spots. Every colony marked a bacterial colony. For L-Top agar assay serial dilutions were made in 1× PBS and then mixed with 5 ml of SeaPlaque Agarose (Biozym Scientific GmbH, Oldendorf) at around 40° C. Dilutions were dropped carefully on LB agar plates. The agar plates were incubated overnight at 37° C. bottom down. The number of bacterial colonies was determined by counting the spots. Every colony marked an infected eucaryotic cell.

Isolation of TAMs. Staining procedures for magnetic cell separation A two-step procedure for labelling of cells with magnetic beads was chosen. First, the cells were labelled with the pan-macrophage anti-F4/80 (IgG, Acris Antibodies GmbH; IgG, Santa Cruz) antibody. Second, the labelled cells are stained with an anti-IgG antibody, labelled with magnetic beads (Miltenyi Biotec GmbH). The total staining time was about 30 min. Antibody labelling of cells was performed at 4° C. for 10-15 min in 1× PBS with 1% bovine serum albumin (BSA) and 0.01% sodium-azide. After one washing with 1× PBS, the cells were incubated with the secondary microbeads labelled antibody. After 10 min incubation at 4° C., unbound particles were first removed by a single washing step. Then mini columns (Miltenyi Biotec GmbH) were placed in a magnetic field of approx. 0.6 Tesla (MACS permanent magnet, Miltenyi Biotec), equilibrated with 500 µl 1× PBS with 1% bovine serum albumin (BSA) and 0.01% sodium-azide and cells are separated. Cells labelled with magnetic beads were retained in a magnetic field and bind to the steelwool fibers. When the column was removed from the external magnetic field, the steelwool readily demagnetizes, the magnetic cells were no longer bound and could be eluted as a single cell suspension.

Preparation of Cells for FACS analysis. Expression of cell surface antigens on tumour cells was analysed by staining with antibodies after treatment with Fcγ/RII/III (2.4G2, BD Bioscience) and flow cytometric analysis using FACScan (BD Immunocytometry Systems). The following monoclonal antibodies were used: fluorescein isothiocynate (FITC)-anti-mouse CD11b (M1/70.15.11.5, Miltenyi Biotec), phycoerythrin (PE)-anti-mouse Gr-1 (RB6-8C5, Miltenyi Biotec) and PE-anti-mouse F4/80 (BM4008R, Acris Antibodies).

Efficacy studies. To explore the therapeutic effect of *Shigella* infection upon tumor growth 1×10$^4$ 4T1 cells were applied s.c. into 28 six- to eight-week-old female Balb/c mice. Tumor growth was determined every other day by a ruler. When tumor volume has reached around 170 mm$^3$ (day 14 post cell implantation), three groups of mice (n=8) were determined by randomization. *Shigella flexneri* M90Tdelta and BS176delta were prepared as described before and 100 µl of the suspension were injected into the lateral tail vein of 4T1 tumor-bearing Balb/c mice. In the naive group 100 µl 1× PBS was applied. Tumor growth was observed every other day. On day 31 post tumor cell implantation the naive and the BS76delta-aroA group and two M90Tdelta-aroA mice were sacrificed and tumor size were compared (data not shown). On day 48 post infection three M90Tdelta-aroA mice were sacrificed to determine the cfu in tumor, liver and spleen tissue. In addition we performed FACS analysis to determine the amount of macrophages in the tumor tissue like described bevor. On day 49 post infection we applied again 1×10$^6$ *Shigella flexneri* M90ΔaroA i.v. On day 68 post first infection cfu was again determined in tumor, liver and spleen tissue. In addition we prepared 2 tumors for histological and immuno-histochemistrial analysis like describes before.

Ex vivo infection of human ascites cells. The ascites cells consist of two different cell populations, on the one hand there are adherent cells and on the other cells there are suspensions cells. The two cell populations were treated as separated cell types. Tumor cells were separated and TAMs were isolated like subscribed before. Ex vivo infection of the three different cell fraction after cell isolation from a patient with wt *S. flexneri* M90T, *S. flexneri* M90Tdelta-aroA and *S. flexneri* BS176delta-aroA. Bacteria grown to logarithmic growth phase were centifuged (4000 rpm, 10 min, 4° C.) and washed with D-MEM medium 3 times. After 1 h of infection at a MOI 100:1, cells were incubated for 1 h with 300 µg/ml gentamicin. After that 50 µg/ml gentamicin were used. 2 hours p.i. cells were harvested to determine cfu or were prepared for Western Blot.

Western Blot analysis. *Shigella*-infected or uninfected cells from six-well cell culture dishes were washed twice with PBS and lysed in 120 µl of 2× Laemmli buffer (1 M Tris-HCl, pH 6.8; Glycerol 86%; β-Mercaptoethanol; 20% SDS, dH$_2$O). Insoluble material was removed by centrifugation (20,000 g, 30 min). For immunoblotting, 10-30 µl of lysates was separated by 10 or 15% SDS-PAGE (Laemmli, U.K. Nature 1970, 227: 680-685) and transferred onto nitrocellulose membranes. After 1 h blocking in 1× PBS supplemented with 5% skimmed milk powder, the membranes were probed with the appropriate primary antibodies (anti-caspase-1 (ICE), from Sigma; anti-cleaved PARP antibody (BD Pharmingen), anti-GAPDH antibody (Chemicon international), anti-β-actin antibody (Sigma) diluted in 5% skimmed milk powder (fraction V; Sigma-Aldrich) in 1× PBS before incubation with peroxidase-conjugated secondary antibodies, detection by an enhanced chemiluminescence (ECL reagents; Amersham Biosciences, UK) and exposed on X-ray film (Kodak, XO-MAT-AR) for 1 to 10 minutes.

Results

Macrophage infiltration has been described in several human tumors including breast (Leek, R. D. et al. Cancer Res 1996, 56: 4625-4629; Leek, R. D., Landers, R. J., Harris, A. L. & Lewis, C. E. Br J Cancer 1999, 79: 991-995; Lewis, J. S., Landers, R. J., Underwood, J. C., Harris, A. L. & Lewis, C. E. J Pathol 2000, 192: 150-158) and ovarian carcinoma (Negus, R. P., Stamp, G. W., Hadley, J. & Balkwill, F. R. Am J Pathol 1997, 150: 11723-1734). To determine the level of infiltrated TAMs in different experimental tumor models macrophages in paraffin embedded tissues of different tumor models (FIG. 1) were stained. In all tumors examined, hotspots of macrophages (brown staining) were detected. Because TAMs are widespread in human breast carcinomas (Kelly, P. M., Davison, R. S., Bliss, E. & McGee, J. O. Br J Cancer 1988, 57: 174-177; Volodlko, N., Reiner, A., Rudas, M. & Jakesz, R. The Breast 1998, 7: 99-105; Lin, E. Y., Nguyen, A. V., Russell, R. G. & Pollard, J. W. J Exp Med 2001, 193: 727-740; Bingle, L., Brown, N. J. & Lewis, C. E. J Pathol 2002, 196: 254-265) and are associated with negative prognosis, 4T1 model and transgenic MMTV-Her2 tumor model were used for further studies.

At the beginning it was sought to investigate the quantitative distribution of *Salmonella* and *Shigella* in the extracellular and intracellular compartment, as well as different cell types of the tumor. Therefore a model was established using grafted (4T1) and spontaneous (MMTV-Her2) tumors. Tumor bearing mice were infected with bacteria and tumors were removed at different time points after infection. Tumor cells were separated to obtain a tumor cell suspension. The tumor cell suspension was treated with/without gentamicin to distinguish extra- and intracellular bacteria. In parallel, cells were separated in macrophages and macrophage depleted fractions to analyze the bacterial content (see FIG. 13). Plating was performed either after lysis of the eukaryotic cells to determine total cfu titers, or by plating in Topagar avoiding cell lysis to determine the number of infected cells.

In a first set of experiments, $1 \times 10^6$ *Salmonella typhimurium* delta-aroA were applied intravenously in mice with established 4T1 (FIG. 2) tumors or spontaneous breast carcinoma (see FIG. 17). As shown in FIG. 2, the strain *Salmonella typhimurium* delta-aroA predominantly targets TAMs in vivo after 4 h and 6 h post infection, although this strain readily infects 4T1 cells in vitro (data not shown). 7 days after infection there were only few bacteria detected in the spleen, which is in line with previous works (Arnold, H. et al. Infect Immun 2004, 72: 6546-6553). After 4 h, 6 h and 7 d significantly more bacteria are found in the macrophages fraction compared to macrophages depleted tumor cells. 4 and 6 hours after infection, most bacteria are intracellular, whereas 7 days after infection 10 fold more bacteria are found extracellularly as determined by cfu numbers derived from gentamicin treated compared to untreated total tumor cells.

Subsequently it was asked whether there is an induction of apoptosis in the macrophages via caspase-1 activation by secreted SipB. In addition one was interested in whether there is a reduction of macrophages in the tumor tissue upon apoptosis. Therefore cell populations for caspase-1 activation and induction of apoptosis after infection with *Salmonella typhimurium* delta-aroA (FIG. 3) were analysed. Caspase-1 activation (FIG. 3a) and PARP cleavage (FIG. 3b) was detectable in total cells and macrophages fractions of tumors from mice 6 hours after infection, but not in the macrophages depleted fraction, where neither caspase-1 processing nor caspase-1 expression was detectable. Caspase-1 induction was not detected in any fraction 7 days after infection. Seven days after infection, the relative amount of TAMs was determined by FACS (FIG. 3c). *Salmonella* did not affect macrophage numbers at this timepoint in comparison to non-infected mice further suggesting that apoptosis induction is transient, or at a minimum, inefficient. A transient apoptosis induction could be explained by the infection biology of *Salmonella*, which express the pathogenicity island SP1 (including SipB) at early timepoints of infection and at later times switch from SP1 to SP2. The SP2 pathogenicity island does not contain virulence factors like SipB which can directly activate caspase-1 processing (Panthel, K. et al. Infect. Immun. 2005, 73: 334-341).

In contrast to *Salmonella Shigella* express IpaB at every timepoint during infection (Schroeder, G. N., Jann, N. J. & Hilbi, H. Microbiology 2007, 153: 2862-2876; Cossart, P. & Sansonetti, P. J. Science 2004, 304: 242-248; Tamano, K. et al. Embo J 2000, 19: 3876-3887). For this reason it was asked whether *Shigella flexneri* also targets TAMs and would be suited to reduce macrophage numbers. In this study the *Shigella flexneri* strains M90T and BS176, the latter being the plasmidless non-virulent variant, were used. To obtain an attenuated strain for animal studies which is not affected in its virulence, a strain was constructed carrying a chromosomal deletion of the aroA-gene locus. In other bacteria such as *Salmonella*, the deletion of the aroA-gene which is important for the generation of aromatic amino acids leads to an attenuation in bacteria (Schafer, R. & Eisenstein, T. K. Infect Immun 1992, 60: 791-797). To allow a genetically defined comparison of growth attenuated virulent and non-virulent strains (Sansonetti, P. J., Kopecko, D. J. & Formal, S. B. Infect Immun 1982, 35: 852-860) it was sought to delete the aroA-locus in the avirulent *Shigella flexneri* strain BS176 and subsequently add the virulence plasmid pWR100 by electroporation. To knockout the aroA-locus in the *Shigella flexneri* BS176 strain the method of Datsenko and Wanner (2000) was applied. The resulting strain, *Shigella flexneri* BS176delta-aroA was termed BS176delta-aroa or BS176delta in the following. Subsequently, the virulence plasmid pWR100, isolated from *Shigella flexneri* M90T, was transformed into the strain BS176delta, resulting in the strain *Shigella flexneri* BS176delta-aroA pWR100. As this strain carries the main features of the virulent strain *Shigella flexneri* M90T, this strain is termed M90Tdelta-aroA or M90Tdelta in the following.

The *Shigella flexneri* BS176delta-aroA pWR100 strain, equivalent to *Shigella flexneri* M90Tdelta-aroA, was deposited at German Collection of Microorganisms and Cell Cultures (DSMZ) under DSM 21058.

After the construction of the aroA-mutants, the strains were characterized with respect to extracellular and intracellular growth, early association, invasion and cell-to-cell spread in vitro (FIG. 4). The plasmidless avirulent strain *Shigella flexneri* BS176 was characterized by a maximal growth rate of 0.3 OD/h in LB medium, whereas the virulent strain *Shigella flexneri* M90T had a slightly reduced maximal growth rate of 0.2 OD/h (FIG. 4a), which might be explained by the presence of the large virulence plasmid pWR100. As expected, strains carrying aroA mutations had substantially reduced maximal growth rates. M90Tdelta-aroA had a 2.5 fold slower maximal growth rate than wt *Shigella flexneri* M90T. Again, BS176delta-aroA had a slightly higher maximal growth rate compared to M90TΔaroA.

Subsequently, the contribution of the aroA mutation with respect to early association, invasion, intracellular replication and cell-to-cell spread was investigated.

As depicted in FIG. 4b, the strain M90Tdelta-aroA showed no significant difference in its rate of association and invasion relative to the wt strain *Shigella flexneri* M90T. In contrast, BS176delta-aroA was attenuated in its invasion behavior as expected.

The wt M90T showed a 12 fold higher intracellular replication rate than the aroA-mutants in the time period of two hours (FIG. 4c). These data show that the strain *Shigella flexneri* M90Tdelta-aroA is strongly attenuated in its intracellular replication as expected.

Because of the defect in intracellular replication of the aroA-mutants, cell-to-cell spread is difficult to assess with a conventional assay. Therefore a new spreading assay was developed, which is less sensitive for intracellular replication (FIG. 4d). In the first step, HeLa-cells were infected for 1 h at a high MOI (multiplicity of infection) of 500:1. Subsequently, the infected cells were irradiated to block the replication of the HeLa cells. The infected, irradiated HeLa cells were co-incubated on a monolayer of non-infected HeLa cells in a ratio of 1:70 in the presence of gentamicin. The number of infected cells was determined by plating on SeaPlaque agarose avoiding cell lysis. As expected, wt M90T showed an increase of the number of infected cells by a factor of 12 after 8 hours. At later time points, the non-attenuated, virulent strain is toxic for the cells and cfu determination is no more possible. In the case of M90Tdelta, the increase of the number of infected cells was 6 fold after 8 hours and 17 fold 12 h after co-infection, whereas the number of infected cells for the avirulent strain BS176delta increased by only 3 fold after 8 h and showed no further increase until 12 h. These results suggest a non-impaired potential of M90Tdelta for cell-to-cell spread. The small increase observed for BS176delta, which does not carry the genetic information for cell-to-cell spread might be due to partial cell lysis at early time points of the highly infected irradiated cells with an only partial killing of extracellular bacteria by the rather low gentamicin concentration of only 10 μg/ml for 12 hours in order to protect the eukaryotic cells. To further examine the characteristics of cellular infection, infected cells were assessed histologically by Giemsa staining (FIG. 4e). The Giemsa stainings of HeLa cells 1 hours (see FIGS. 11) and 4 hours after infection (FIG. 4e) showed that bacteria of the strains M90T and M90Tdelta are mainly located at cell-cell-contacts. There is also cell-to-cell spread detectable. In contrast, there are nearly no intracellular bacteria of the strain BS176delta detectable even after 4 h p.i. In addition, there is no sign of cell-to-cell spread for the avirulent strain.

To determine the capacity of the aroA-mutants to induce caspase-1 activation (FIG. 4f) and apoptosis induction (FIG. 4g), J774A.1 mouse macrophages were infected and cellular lysates were analyzed. M90Tdelta, but not BS176delta, could induce both caspase-1 induction and apoptosis. Of note, apoptosis induction by M90Tdelta was caspase-1 dependent, as the caspase-1 specific inhibitor YVAD-CHO fully blocked caspase-1 and PARP processing (FIGS. 4f and 4g).

Subsequently it was analysed whether *Shigella* show a similar preferred targeting of macrophages as observed for *Salmonella*. Therefore, *Shigella* i.v. in Balb/c mice were injected with established 4T1-tumors (FIG. 5 and FIG. 16) in a similar setting as performed before for *Salmonella*. Again, significantly more bacteria per cell (FIG. 5a, b) and more infected cells (FIG. 5b, d) were found in the macrophages fraction at any timepoint. Furthermore, the major part of M90Tdelta-aroA is found intracellularly (FIG. 5a, b), whereas 50 fold more bacteria were found extracellularly 6 hours after infection with the avirulent strain BS176delta-aroA (FIG. 5a).

It was also analysed the fractions for caspase-1 expression and activation and induction of apoptosis (FIG. 6 and FIGS. 20). 4 h, 6 h and 7 d after infection caspase-1 activation (FIG. 6a) and PARP cleavage (FIG. 6b) was analyzed by Western Blot. Caspase-1 activation and PARP cleavage was detectable in total cells and macrophages fractions of tumors taken from mice 4 and 6 hours, and in the macrophages fraction 7 days after infection for M90Tdelta, but not BS176delta. In addition, 7 days after infection, the relative amount of tumor-associated macrophages was determined by FACS (FIG. 6c).

M90Tdelta, but not BS176delta infection resulted in a substantial reduction of macrophage numbers in tumor bearing Balb/c mice and also in MMTV-Her2 mice (supplementary data) (Lin, E. Y., Nguyen, A. V., Russell, R. G. & Pollard, J. W. J Exp Med 2001, 193: 727-740; Bingle, L., Brown, N. J. & Lewis, C. E. J Pathol 2002, 196: 254-265; Scholl, S. M., Crocker, P., Tang, R., Pouillart, P. & Pollard, J. W. Mol Carcinog 1993, 7: 207-211; Kirma, N. et al. Cancer Res 2004, 64: 4162-4170; Gouon-Evans, V., Rothenberg, M. E. & Pollard, J. W. Development 2000, 127: 2269-2282; Pollard, J. W. & Hennighausen, L. Proc Natl Acad Sci U S A 1994, 91: 9312-9316; Van Nguyen, A. & Pollard, J. W. Dev Biol 2002, 247: 11-25; Pollard, J. W. Nat Rev Cancer 2004, 4: 71-78; Murdoch, C., Giannoudis, A. & Lewis, C. E. Blood 2004, 104: 2224-2234; Filderman, A. E., Bruckner, A., Kacinski, B. M., Deng, N. & Remold, H. G. Cancer Res 1992, 52:3661-3666)

Histological examination of naïve (FIG. 6e, upper panel), BS176delta (FIG. 6e, middle panel) and M90Tdelta (FIG. 6e, lower panel) infected mice confirmed the substantial reduction of macrophages and a disruption of macrophage agglomerations (e, anti-F480 staining, left panels) and showed an intense inflammation (e, anti-CD45 staining, right panels) in tumors derived from M90Tdelta, but not naive or BS176delta infected mice 7 days after infection.

To investigate whether this substantial reduction in macrophage numbers and marked inflammation induced by M90Tdelta is associated with a therapeutic effect, bacteria were applied to tumor bearing Balb/c mice and tumor growth was assessed (FIG. 7a). Infection with BS176delta resulted in a small, albeit significant reduction of tumor growth. In contrast, a single i.v. infection with M90Tdelta resulted in a substantial and significant reduction in tumor growth. Of note, tumor growth was completely blocked 19 days after treatment. The non-growing tumors exhibited very low macrophage (3-4%) numbers and bacteria were not detectable 48 days after infection (FIG. 7c). On day 49 $1 \times 10^6$ bacteria were applied i.v. in the remaining 3 mice. No further reduction of tumor size was detected. On day 68 cfu was determined and histological examinations followed. No bacteria were detectable in tumor, liver and spleen (data not shown).

To investigate whether a treatment with *Shigella flexneri* M90Tdelta-aroA would be applicable in humans cells derived from freshly isolated ascites from a ovarian carcinoma patient were infected with M90Tdelta-aroA (FIG. 8a and see FIG. 20). M90Tdelta-aroA effectively infected TAMs isolated from human tumors and induced caspase-1 processing and apoptosis in these cells (FIG. 8b). Again, infection of TAMs derived from a human tumor isolate was at least 100× more efficient compared to the macrophage depleted fraction.

Example 2

Expression and Secretion of the ipaB-gene (NC_004851) of *Shigella flexneri* in Gram Negative Bacteria (*Escherichia coli* K12)

2a) Cloning of ipaB-gene (NC 004851) of *Shigella flexneri* in Secretion Plasmid

*Salmonella* can like *Shigella* induce inflammation and apoptosis of infected macrophages through activation of caspase-1 mediated by the SipB protein, which is secreted via type III secretion systems (TTSS) (Suzuki, T. et al. J Biol Chem 2005, 280: 14042-14050; Zychlinsky, A. et al. Mol Microbiol 1994, 11: 619-627; Chen, L. M. et al., Mol Microbiol 1996, 21: 1101-1115; Hilbi, H. et al. J. Biol. Chem. 1998, 273: 32895-32900). *Salmonella* activate caspase-1 by SipB and induce apoptosis in TAMs at early, but not late timepoints and failed to reduce the relative amounts of TAMs. In contrast, metabolically attenuated, virulent *Shigella* strains, but not avirulent *Shigella* strains, are able to activate caspase-1 and induce apoptosis in TAMs by IpaB at all timepoints in the 4T1 and the spontaneous breast cancer model.

A transient apoptosis induction by *Salmonella* could be explained by expression of the pathogenicity island SPI1 (including SipB) at early timepoints of infection and at later times switch from SPI1 to SPI2. The SPI2 pathogenicity island does not contain virulence factors like SipB which can directly activate caspase-1 processing (Panthel, K. et al. Infect. Immun. 2005, 73: 334-341). In contrast to *Salmonella*, *Shigella* express IpaB at every timepoint during infection (Schroeder, G. N., et al., Microbiology 2007, 153: 2862-2876; Cossart, P. & Sansonetti, P. J. Science 2004, 304: 242-248; Tamano, K. et al. Embo J 2000, 19: 3876-3887).

To evaluate the possibility to functionally express and secrete functional ipaB in a Gram negative strain, the ipaB gene was cloned into the pMoHly expression vector leading to the expression and secretion of the ipaB protein. The secretion is mediated by the plasmid encoded type I hemolysin secretion system (T1SS) of *Escherichia coli*. The secretion plasmid was previously described and is effective in a large variety of Gram negative purpose. As a prove of concept, cloning into an *Escherichia coli* strain was performed.

In the following, the construction of a *Escherichia coli* K12 strain encompassing the type I secretion system for secretion of ipaB is described. In principle, any attenuated facultative intracellular gram negative strain can be used for this purpose.

The ipaB gene was cloned in the Type I delivery plasmid pMOhIy$_{kan}$. A single NsiI restriction site was located between the two residual sequences of the hIyA gene for the in-frame insertion sequences determining the heterologous protein (Fensterle et al. Cancer Gene Therapy 2008). For insertion of sequences containing a NsiI restriction site a new polylinker was established in pMOhIy$_{kan}$. Following restriction sites were used for the enlarged multiple cloning sit (mcs): XhoI, PvuI, NheI and KpnI.

Oligonucleotides (CGGTACCGCTAGCCGATCGCTC-GAGATGCA (SEQ ID NO:13) and TCTCGAGCGATCG-GCTAGCGGTACCGTGCA (SEQ ID NO:14)) containing the sequence of the restriction sites with an overhang complementary to NsiI site (5'-TGCA-3') were annealed to create a sequence section with the inserted restriction sites. After annealing of this resulting double strand DNA section the polylinker was inserted in the NsiI digested pMOhIy$_{kan}$ resulting in the new plasmid pMOhIy$_{kan}$ mcs. Afterwards antibiotic resistant clones were screened. Correct insertion of the mcs was confirmed by restriction enzyme digestion and sequencing.

The coding sequence of ipaB contains a NsiI restriction site at position 1,138 (bp). Therefore the freshly constructed pMOhIy$_{kan}$ mcs was used to insert the open reading frame of ipaB. The ipaB gene was amplified by PCR with the primers Salm: mcs ipaB XhoI hin (AAAAAACTCGAGATGCAT-AATGTAAGCACCAC (SEQ ID NO:15)) and Salm: mcs ipaB KpnI rück (AAAAAAGGTACCTCAAGCAG-TAGTTTGTTGC (SEQ ID NO:16)). The forward primer was designed to create a XhoI restriction site and the reverse primer a KpnI site. The PCR product and pMOhIy$_{kan}$ mcs were digested by XhoI and KpnI and afterwards ipaB was inserted in pMOhIy$_{kan}$ mcs by ligation. Screening of antibiotic resistant clones was done by PCR and insertion was affirmed by sequencing. The plasmid called pMOhIipa of the sequenced clone was isolated by Mini Prep and used for further studies (FIG. 22).

The plasmid was transformed in *E. coli* DH5a and assessed for functionality. FIG. 23 shows the successful expression and secretion of the fusion protein by the recombinant *E. coli* strain. IpaB expression by *E. coli* pMOhIipa and *E. coli* ΔToIC pMOhIipa showed a product of 70 kDa, because the cloned IpaB was fused with a C-terminal HIyA secretion signal in the pMOhIy$_{kan}$ model. IpaB was detected in the M90T lysate, in pellet and in supernatant of *E. coli* pMOhIipa. In the supernatant of *E. coli* ΔToIC pMOhIipa there was no IpaB detectable, as this strain lacks the toIC gene which is required for the function of the *E. coli* type I secretion machinery.

To investigate whether caspase-1 is activated by different *E. coli* DH5α strains RAW 264.7 macrophages were infected and Western Blot analysis was performed after different time points p.i. (FIG. 24).

Western Blot analysis showed that *E. coli* pMOhIipa strain activated caspase-1 in RAW 264.7 macrophages (FIG. 24). In addition *E. coli* ΔToIC pMOhIipa showed a very diminished caspase-1 activation 6 h p.i. The Western Blot analysis was performed 2 times and this result was always determined and it could be a technical problem because of the caspase-1 activation through *E. coli* ΔToIC pMOhIipa. *E. coli* pMOhIipa activated caspase-1 3 h p.i., but in comparison to the M90T control the caspase-1 activation was quite reduced. Not infected RAW 264.7 macrophages were used as negative control. RAW 264.7 macrophages infected by *E. coli* ΔToIC showed no caspase-1 activation but the zymogen of caspase-1.

In the next step, the efficacy of the system was assessed in vivo. As TAMs are deficient in the uptake of non-invasive bacteria (see results for BS176, data not shown for *E. coli*), we assessed the capacity of *E. coli* ΔToIC pMOhIipa to induce apoptosis in splenic macrophages after IV application. As shown in FIG. 25, *E. coli* ΔToIC pMOhIipa successfully induces caspase-1 processing in splenic macrophages, proving that the system is effective in vivo.

To affect TAMs, the system has to be transferred into invasive Gram negative bacteria including, but not limited to, *Shigella, Salmonella* and invasive *E. coli* strains. The functionality of the system in inducing caspase-1 processing in macrophages after IV application together with the demonstration that invasive, ipaB expressing *Shigella* can induce apoptosis in TAMs will lead to a recombinant bacterium for targeted depletion of macrophages according to this system.

2b) Cloning of ipaB-gene of *Shigella flexneri* in Gram Positive Bacteria (*Listeria monocytogenes* EGDe)

Data on caspase-1 activation by Listeria is conflicting and caspase-1 and apoptosis induction within macrophages is, at least, less efficient compared to *Shigella* (Cervantes, J. et al., Cell Microbiol 2008, 10: 41-52; Franchi, L. et al., J Biol Chem 2007, 282: 18810-18818). However, *Listeria* are intracellular bacteria, target macrophages within tumors and thus (Singh, R. & Paterson, Y. Expert Rev Vaccines 2006. 5: 541-552) might be suitable for a macrophage targeted bacterial tumor therapy. To achieve sustained apoptosis induction, an attenuated Listeria strain with constitutive expression and secretion of ipaB is being constructed.

For expression of IpaB in *Listeria monocytogenes* EGDe ΔaroA the listerial promoter from the actA gene (PactA) was used. For the secretion of IpaB in *Listeria monocytogenes* EGDe ΔaroA the secretion signal of listeriolysin (SShly) was fused to the 3' end of the promoter. PactA was amplified by PCR from genomic DNA isolated from Listeria monocytogenes EGD with following primers: PactA PstI NcoI hin (TATCGACTGCAGCCATGGGAGCTCGCG-GCCGCTGAA (SEQ ID NO:17)) as forward primer and as reverse primer: PactA overhang rück (CTAGCAT-TATTTTTTTCATTTATACTCCCTCCTCGTGATACGC (SEQ ID NO:18)). The reverse primer was designed with an overhang complementary to the sequence from the secretion signal SShly. And the secretion signal was amplified by following primers: SS hly overhang hin (GCGTATCACGAG-GAGGGAGTATAAATGAAAAAAATAATGCTAG (SEQ ID NO:19)) and SS hly BamHI rück (AAAAAAGGATC-CATCCTTTGCTTCAGTTTG (SEQ ID NO:20)). Afterwards recombinant PCR was performed with the amplified PCR products of PactA SShly and by following primers: PactA PstI NcoI hin (forward) and SS hly BamHI rück (reverse). Afterwards the product PactA+SShly of recombinant PCR and the plasmid pUC18 were digested by the restriction enzymes PstI and BamHI. Adjacent PactA+SShly was inserted by ligation in pUC18 and appropriate insertion was affirmed by restriction enzyme digestion and sequencing. Due to the reverse primer of SShly a BamHI restriction site was integrated. Accordingly ipaB was amplified by PCR with primers creating the respective restriction sites BamHI at the start and SacI at the end: ipaB BamHI hin (AAAAAAG-GATCCATGCATAATGTAAGCACCAC (SEQ ID NO:21)) and ipaB SacI rück (AAAAAAGAGCTCTCAAGCAG-TAGTTTGTTGC (SEQ ID NO:22)). Then the ipaB gene was seamlessly cloned behind the signal sequence in pUC18 and it was sequenced.

Subsequently the construct PactA+SShly+ipaB was cut out of pUC18 by the restriction enzymes PstI and SacI and inserted in the PstI and SacI digested gram$^+$ expression vector pSP0 by ligation resulting in the new plasmid pSPR17 (FIG. 26

```
<213> ORGANISM: Artificial Sequence
<220> FEATURE:
<223> OTHER INFORMATION: synthetic oligo

<400> SEQUENCE: 5
ttatacgcaa ggcgacaagg                                               20

<210> SEQ ID NO 6
<211> LENGTH: 20
<212> TYPE: DNA
<213> ORGANISM: Artificial Sequence
<220> FEATURE:
<223> OTHER INFORMATION: synthetic oligo

<400> SEQUENCE: 6
gatcttccgt cacaggtagg                                               20

<210> SEQ ID NO 7
<211> LENGTH: 20
<212> TYPE: DNA
<213> ORGANISM: Artificial Sequence
<220> FEATURE:
<223> OTHER INFORMATION: synthetic oligo

<400> SEQUENCE: 7
cagtcatagc cgaatagcct                                               20

<210> SEQ ID NO 8
<211> LENGTH: 20
<212> TYPE: DNA
<213> ORGANISM: Artificial Sequence
<220> FEATURE:
<223> OTHER INFORMATION: synthetic oligo

<400> SEQUENCE: 8
cggtgccctg aatgaactgc                                               20

<210> SEQ ID NO 9
<211> LENGTH: 20
<212> TYPE: DNA
<213> ORGANISM: Artificial Sequence
<220> FEATURE:
<223> OTHER INFORMATION: synthetic oligo

<400> SEQUENCE: 9
gatgcaggcc aagaggttag                                               20

<210> SEQ ID NO 10
<211> LENGTH: 17
<212> TYPE: DNA
<213> ORGANISM: Artificial Sequence
<220> FEATURE:
<223> OTHER INFORMATION: synthetic oligo

<400> SEQUENCE: 10
gcgttgatga ccgcatc                                                  17

<210> SEQ ID NO 11
<211> LENGTH: 19
<212> TYPE: DNA
<213> ORGANISM: Artificial Sequence
<220> FEATURE:
<223> OTHER INFORMATION: synthetic oligo

<400> SEQUENCE: 11
gatttctacc gcaatgacg                                                19
```

<210> SEQ ID NO 12
<211> LENGTH: 19
<212> TYPE: DNA
<213> ORGANISM: Artificial Sequence
<220> FEATURE:
<223> OTHER INFORMATION: synthetic oligo

<400> SEQUENCE: 12
ggaaacaagt gagcgtttc                                                    19

<210> SEQ ID NO 13
<211> LENGTH: 30
<212> TYPE: DNA
<213> ORGANISM: Artificial Sequence
<220> FEATURE:
<223> OTHER INFORMATION: synthetic oligo

<400> SEQUENCE: 13
cggtaccgct agccgatcgc tcgagatgca                                        30

<210> SEQ ID NO 14
<211> LENGTH: 30
<212> TYPE: DNA
<213> ORGANISM: Artificial Sequence
<220> FEATURE:
<223> OTHER INFORMATION: synthetic oligo

<400> SEQUENCE: 14
tctcgagcga tcggctagcg gtaccgtgca                                        30

<210> SEQ ID NO 15
<211> LENGTH: 32
<212> TYPE: DNA
<213> ORGANISM: Artificial Sequence
<220> FEATURE:
<223> OTHER INFORMATION: synthetic oligo

<400> SEQUENCE: 15
aaaaaactcg agatgcataa tgtaagcacc ac                                     32

<210> SEQ ID NO 16
<211> LENGTH: 31
<212> TYPE: DNA
<213> ORGANISM: Artificial Sequence
<220> FEATURE:
<223> OTHER INFORMATION: synthetic oligo

<400> SEQUENCE: 16
aaaaaaggta cctcaagcag tagtttgttg c                                      31

<210> SEQ ID NO 17
<211> LENGTH: 36
<212> TYPE: DNA
<213> ORGANISM: Artificial Sequence
<220> FEATURE:
<223> OTHER INFORMATION: synthetic oligo

<400> SEQUENCE: 17
tatcgactgc agccatggga gctcgcggcc gctgaa                                 36

<210> SEQ ID NO 18
<211> LENGTH: 43
<212> TYPE: DNA
<213> ORGANISM: Artificial Sequence
<220> FEATURE:
<223> OTHER INFORMATION: synthetic oligo -continued

```
<400> SEQUENCE: 18
ctagcattat tttttcatt tatactccct cctcgtgata cgc                      43

<210> SEQ ID NO 19
<211> LENGTH: 43
<212> TYPE: DNA
<213> ORGANISM: Artificial Sequence
<220> FEATURE:
<223> OTHER INFORMATION: synthetic oligo

<400> SEQUENCE: 19
gcgtatcacg aggagggagt ataaatgaaa aaaataatgc tag                     43

<210> SEQ ID NO 20
<211> LENGTH: 30
<212> TYPE: DNA
<213> ORGANISM: Artificial Sequence
<220> FEATURE:
<223> OTHER INFORMATION: synthetic oligo

<400> SEQUENCE: 20
aaaaaaggat ccatcctttg cttcagtttg                                    30

<210> SEQ ID NO 21
<211> LENGTH: 32
<212> TYPE: DNA
<213> ORGANISM: Artificial Sequence
<220> FEATURE:
<223> OTHER INFORMATION: synthetic oligo

<400> SEQUENCE: 21
aaaaaaggat ccatgcataa tgtaagcacc ac                                 32

<210> SEQ ID NO 22
<211> LENGTH: 31
<212> TYPE: DNA
<213> ORGANISM: Artificial Sequence
<220> FEATURE:
<223> OTHER INFORMATION: synthetic oligo

<400> SEQUENCE: 22
aaaaaagagc tctcaagcag tagtttgttg c                                  31
```

The invention claimed is:

1. A method of treating a mammal suffering from a physiological and/or pathophysiological condition, the method comprising non-orally administering at least one non-pathogenic and/or attenuated bacterium, wherein said non-pathogenic and/or attenuated bacterium is capable of inducing apoptosis in a tumor-associated macrophage (TAM);
wherein
(a) apoptosis is induced in tumor-associated macrophages (TAM) and tumor-associated macrophages (TAM) are partially or nearly completely depleted and/or
(b) apoptosis is induced in disease-associated macrophages and disease associated macrophages are partially or nearly completely depleted,
wherein the at least one bacterium constitutively expresses IpaB, SipB, or a combination thereof.

2. The method according to claim 1, wherein the at least one bacterium is selected from the group consisting of gram-negative bacterium and gram-positive bacterium.

3. The method according to claim 1, wherein the at least one bacterium is selected from the group consisting of *Shigella* spp., *Salmonella* spp., *Listeria* spp., *Mycobacterium* spp., *Escherichia* spp., *Yersinia* spp., *Vibrio* spp., and *Pseudomonas* spp..

4. The method according to claim 1, wherein the at least one bacterium is selected from the group consisting of *Shigella flexneri, Salmonella typhimurium, Mycobacterium bovis BCG, Listeria monocytogenes, Escherichia coli, Salmonella typhi, Yersinia enterocolitica*, and *Vibrio cholerae*.

5. The method according to claim 1, wherein the at least one bacterium is attenuated in its virulence either by a loss of function in at least one virulence factor necessary for infection of the host, by an auxotrophic mutation leading to an impaired growth in a host, or a combination thereof.

6. The method according to claim 1, wherein the attenuation of at least one bacterium is caused by deletion or inactivation of at least one gene selected from the group consisting of aroA, aro, asd, gal, pur, cya, crp, phoP/Q, and omp.

7. The method according to claim 1, wherein the macrophages are M1 macrophages, M2 macrophages, or a combination thereof.

8. The method according to claim 1, wherein the macrophages are M2 macrophages.

9. The method according to claim 1, wherein the induction of apoptosis is achieved by caspase activation.

10. The method according to claim 1, wherein the at least one bacterium is a recombinant bacterium.

11. The method according to claim 1, wherein the at least one bacterium comprises at least one chromosomally integrated DNA encoding at least one protein selected from the group of IpaB and SipB.

12. The method according to claim 11, wherein the chromosomally integrated DNA is a recombinant DNA.

13. The method according to claim 1, wherein the at least one bacterium comprises at least one chromosomal deletion or inactivation of at least one regulatory DNA leading to the constitutive expression of at least one protein selected from the group of IpaB and SipB.

14. The method according to claim 1, wherein the at least one bacterium comprises at least one plasmid wherein the at least one plasmid encodes IpaB, SipB, or a combination thereof.

15. The method according to claim 14, wherein the at least one plasmid encodes at least one regulatory DNA leading to the constitutive expression of IpaB, SipB, or a combination thereof.

16. The method according to claim 1, wherein the at least one bacterium is selected from the group consisting of: *Shigella flexneri* M90T delta-aroA, *Salmonella typhimurium* delta-aroA, and *Shigella flexneri* BS 176 delta-aroA pWR100.

17. The method according to claim 1, wherein the at least one bacterium is provided in lyophilized form.

18. The method according to claim 1, wherein the at least one bacterium is provided in a pharmacologically acceptable buffer for intravenous injection.

19. The method according to claim 1, wherein the physiological and/or pathophysiological condition to be treated is selected from the group consisting of a disease involving macrophage inflammation where macrophages are associated with disease onset or disease progression, a tumor disease, uncontrolled cell division, a malignant tumor, a benign tumor, a solid tumor, a sarcoma, a carcinoma, a hyperproliferative disorder, a carcinoid, Ewing sarcoma, Kaposi sarcoma, a brain tumor, a tumor originating from the brain, a tumor originating from nervous system, a tumors originating from the meninge, a glioma, a neuroblastoma, stomach cancer, kidney cancer, kidney cell carcinomas, prostate cancer, a prostate carcinoma, a connective tissue tumor, a soft tissue sarcoma, a pancreatic tumor, a liver tumor, a head tumor, a neck tumor, oesophageal cancer, thyroid cancer, osteosarcoma, retinoblastoma, thymoma, testicular cancer, lung cancer, bronchial carcinomas, breast cancer, mamma carcinomas, intestinal cancer, a colorectal tumor, colon carcinoma, rectum carcinoma, gynecological tumor, ovarian tumor, uterine cancer, cervical cancer, cervix carcinoma, cancer of the body of the uterus, a corpus carcinoma, an endometrial carcinoma, urinary bladder cancer, bladder cancer, skin cancer, basalioma, spinalioma, melanoma, intraocular melanoma, leukemia, chronic leukemia, acute leukemia, lymphoma, infection, viral infection, bacterial infection, influenza, chronic inflammation, organ rejection, an autoimmune disease, diabetes and diabetes type II.

20. The method according to claim 1, wherein the bacterium is administered before and/or during and/or after administering at least one further pharmacologically active substance.

21. The method according to claim 20, wherein the further pharmacologically active substance is selected from the group consisting of: a DNA topoisomerase I inhibitor, a DNA topoisomerase II inhibitor, a DNA intercalator, an alkylating agent, a microtubuli destabilizer, a hormone receptor agonist, a growth factor receptor agonist, a hormone receptor antagonist, a growth factor receptor agonist, an inhibitor of signal transduction, an antibody against a growth factor, an antibody against a growth factor receptor, a kinase inhibitor, and an antimetabolite.

22. The method according to claim 20, wherein the further pharmacologically active substance is selected from the group consisting of actinomycin D, aminoglutethimide, asparaginase, Bevacizumab, azathioprine, BCNU (carmustine), bleomycin, busulfan, carboplatin, CCNU (lomustine), chlorambucil, cisplatin, colaspase, cyclophosphamide, cytarabine, dactinomycin, daunorubicin, diethylstilbestrol, doxorubicin (adriamycin), DTIC (dacarbacin), epirubicin, Cetuximab, erythrohydroxynonyladenine, ethynyloestradiol, etoposide, fludarabine phosphate, fluoxymesterone, flutamide, gemcitabine, Imatinib, trastuzumab, hexamethylmelamine, hydroxyurea, hydroxyprogesterone caproate, idarubicin, ifosfamide, interferon, Gefitinib, irinotecan, L-asparaginase, leucovorin, mechlorethamine, medroxyprogesterone acetate, megestrol acetate, melphalan, mesna, methotrexate, mitomycin C, mitotane, mitoxantrone, N-phosphonoacetyl-L-aspartate (PALA), oxaliplatin, pentostatin, plicamycin, prednisolone, prednisone, procarbazine, raloxifen, rapamycin, semustine, sorafenib, streptozocin, tamoxifen, Erlotinib, Docetaxel, teniposide, testosterone propionate, thioguanine, thiotepa, topotecan, trimethylmelamine, uridine, vinblastine, vincristine, vindesine, vinorelbine, 2',2'-difluorodeoxycytidine,5-fluorodeoxyuridine monophosphate,5-azacytidine cladribine,5-fluorodeoxyuridine, 5-fluorouarcil (5-FU), and 6-mercaptopurine.

23. The method according to claim 1, wherein the at least one bacterium is administered before, during, after or a combination thereof after treating with radiotherapy, surgery, or a combination thereof.

* * * * *